US007309583B2

(12) United States Patent
Walker et al.

(10) Patent No.: US 7,309,583 B2
(45) Date of Patent: Dec. 18, 2007

(54) HOMOLOGOUS 28-KILODALTON IMMUNODOMINANT PROTEIN GENES OF *EHRLICHIA CANIS* AND USES THEREOF

(75) Inventors: David H. Walker, Galveston, TX (US); Xue-Jie Yu, Houston, TX (US); Jere W. McBride, Galveston, TX (US)

(73) Assignee: Research Development Foundation, Carson City, NV (US)

( * ) Notice: Subject to any disclaimer, the term of this patent is extended or adjusted under 35 U.S.C. 154(b) by 1011 days.

(21) Appl. No.: 10/062,920

(22) Filed: Jan. 31, 2002

(65) Prior Publication Data
US 2003/0096250 A1 May 22, 2003

Related U.S. Application Data

(60) Division of application No. 09/660,587, filed on Sep. 12, 2000, now Pat. No. 6,392,023, which is a continuation-in-part of application No. 09/261,358, filed on Mar. 3, 1999, now Pat. No. 6,403,780, which is a continuation-in-part of application No. 09/201,458, filed on Nov. 30, 1998, now Pat. No. 6,458,942.

(51) Int. Cl.
C12P 21/06 (2006.01)
C07K 14/00 (2006.01)
(52) U.S. Cl. .................. 435/69.1; 530/350; 514/2
(58) Field of Classification Search ............... 435/69.1; 530/350; 514/2
See application file for complete search history.

(56) References Cited

U.S. PATENT DOCUMENTS

| 5,843,460 | A | 12/1998 | Labigne et al. |
| 6,043,085 | A | 3/2000 | Yu et al. ............. 435/325 |
| 6,392,023 | B1 | 5/2002 | Walker et al. ........... 536/23.1 |
| 6,403,780 | B1 | 6/2002 | Walker et al. ........... 536/23.1 |

FOREIGN PATENT DOCUMENTS

| WO | WO 98/16554 | 4/1998 |
| WO | WO 99/13720 | 3/1999 |
| WO | WO 00/32745 | 6/2000 |

OTHER PUBLICATIONS

Ohashi et al. Cloning and Characterization of Multigenes Encoding the Immunodominant 30-Kilodalton Major Outer Membrane Proteins of *E. canis* and Application of the Recombinant Protein for Serodiagnosis. Sep. 1998, J. Clin. Microbiol. 36(9): 2671-2680.*
McBride et al. Molecular Cloning of the Gene for a Conserved Major Immunoreactive 28-Kilodalton Protein of *E. canis*: a Potential Serodiagnostic Antigen. May 1999, Clin. Diag. Lab. Immunol. 6(3): 392-399.*
Ohashi et al. Immunodominant Major Outer Membrane Proteins of *Ehrlichia chaffeensis* are Encoded by a Polymorphic Multigene Family. Jan. 1998, Infect. Immun. 66(1): 132-139.*

Arturo Casadevall, Antibody-Mediated Immunity against Intracellular Pathogens: Two-Dimensional Thinking comes Full Circle Aug. 2003, vol. 71, No. 8, pp. 4225-4228.*
Anderson et al., "*Ehrlichia chaffeensis*, a new species associated with human ehrlichiosis," *J Clin Microbiol*, 29(12):2838-2842, 1991.
Anderson et al., "*Ehrlichia ewingii* sp. Nov., the etiologic agent of canine *Granulocytic ehrlichiosis*" *Int J Syst Bacteriol*, 42(2):299-302, 1992.
Brouqui et al., "Antigenic characterization of ehrlichiae: protein immunoblotting of *Ehrlichia canis*, *Ehrlichia sennetsu*, and *Ehrlichia risticii*," *J Clin Microbiol*, 30(5):1062-1066, 1992.
Burgess et al., "Possible dissociation of the heparin-binding and mitogenic activities of heparin-binding (acidic fibroblast) growth factor-1 from its receptor-binding activities by site-directed mutagenesis of a single lysine residue," *J. Cell. Bio.*, 111:2129-2138, 1990.
Chen et al., "Identification of the antigenic constituents of *Ehrlichia chaffeensis*," *Am J Trop Med Hyg*, 50(1):52-58, 1994.
Chen et al., "Western immunoblotting analysis of the antibody responses of patients with human *Monocytotropic ehrlichiosis* to different strains of *Ehrlichia chaffeensis* and *Ehrlichia canis*," *Clin Diag Lab Immunol*, 4(6):731-735, 1997.
Dawson et al., "Serologic diagnosis of human ehrlichiosis using two *Ehrlichia canis* isolates," *J Infect Dis*, 163:564-567, 1991.
GenBank Accession No. AAY069965; Dec. 12, 2001.
GenBank Accession No. AF078553.
GenBank Accession No. AF082744.
GenBank Accession No. AF230642.
GenBank Accession No. U72291.
GenBank Accession No. AAK28699.
GenBank Accession No. AAC68666.
GenBank Accession No. AF078555.
Groves et al., "Transmission of *Ehrlichia canis* to dogs by ticks (*Rhipicephalus sanguineus*)," *Am J Vet Res*, 36:937-940, 1975.
Harrus et al., "Amplification of ehrlichial DNA from dogs 34 months after infection with *Ehrlichia canis*," *J Clin Microbiol*, 36(1):73-76, 1998.
Jobling et al., "Analysis of structure and function of the B subunit of cholera toxin by the use of site-directed mutagenesis," *Mol. Microbiol.*, 5:1755-1767, 1991.

(Continued)

*Primary Examiner*—Karen Cochrane Carlson
*Assistant Examiner*—Holly Schnizer
(74) *Attorney, Agent, or Firm*—Fulbright & Jaworski, LLP

(57) ABSTRACT

The present invention is directed to the cloning, sequencing and expression of homologous immunoreactive 28-kDa protein genes, p28-1, -2, -3, -5, -6, -7, -9, from a polymorphic multiple gene family of *Ehrlichia canis*. Further disclosed is a multigene locus encoding all nine homologous 28-kDa protein genes of *Ehrlichia canis*. Recombinant *Ehrlichia canis* 28-kDa proteins react with convalescent phase antiserum from an *E. canis*-infected dog, and may be useful in the development of vaccines and serodiagnostics that are particularly effective for disease prevention and serodiagnosis.

3 Claims, 20 Drawing Sheets

OTHER PUBLICATIONS

Jongejan et al., "The immunodominant 32-kilodalton protein of *Cowdria ruminantium* is conserved within the genus *Ehrlichia*," *Rev Elev Med Vet Pays Trop*, 46(1-2):145-152, 1993.

McBride et al., "A conserved, transcriptionally active p28 multigene locus of *Ehrlichia canis*," Gene, 254:245-252, 2000.

McClure, "Mechanism and control of transcription initiation in prokaryotes," *Ann Rev Biochem*, 54:171-204, 1985.

Pharmacia Biotech, *BioDirectory*, Chapter 9, 217-236, 1996.

Reddy et al., "Molecular characterization of a 28 kDa surface antigen gene family of the tribe Ehrlichiae," *Biochem Biophys Res Comm*, 247(3):636-643, 1998.

Rikihisa et al., "Western immunoblot analysis of *Ehrlichia chaffeensis*, *E. canis*, or *E. ewingii* infections in dogs and humans," *J Clin Microbiol*, 32(9):2107-2112, 1994.

Shankarpappa, "Antigenic and genomic relatedness among *Ehrlichia resticii*, *Ehrlichia sennetsu*, and *Ehrlichia canis*," *Int J Syst Bacteriol*, 42(1):127-132, 1992.

Storey et al., "Molecular cloning and sequencing of three granulocytic Ehrlichia genes encoding high-molecular-weight immunoreactive proteins," *Infection and Immunity*, 66(4):1356-1363, 1998.

Yu et al., "Characterization of the complete transcriptionally active *Ehrlichia chaffeensis* 28 kDa outer membrane protein multigene family," *Gene*, 248:59-68, 2000.

Yu et al., "Detection of *Ehrlichia chaffeensis* in human tissue by using a species-specific monoclonal antibody," *J. Clin Microbiol.* 31:3284-3288, 1993.

Database EMBL Online, "*Ehrlichia canis* major outer membrane protein P30 multigene cluster 1, complete sequence," XP002346095, Oct. 28, 1998 [abstract].

Database UniProt Online, "P28-2 (Major outer membrane protein P30-10)." XP002346097, Mar. 1, 2001 [abstract].

Database UniProt Online, "P28-9." XP002346099, Mar. 1, 2001 [abstract].

Database UniProt Online, "P28-3 (Major outer membrane protein P30-4)." XP002346098, Mar. 1, 2001 [abstract].

Database UniProt Online, "P28-1 (Major outer membrane protein P30-5)." XP002346096, Mar. 1, 2001 [abstract].

Database EMBL Online, "*Ehrlichia canis* p28 multigene locus, partial sequence," XP002346094, Oct. 20, 1998 [abstract].

Reddy et al., "Molecular Characterization of a 28 kDa Surface Antigen Gene Family of the Tribe Ehrlichiae," *Biochem. Biophys. Res. Comm.*, 247:636-643, 1998.

* cited by examiner

```
  1 ATTTTATTTATTACCAATCTTTATATATAATATATTAAATTTCTCTTACAAAAATCTCTAATG    60
 61 TTTTATACCTAATATATATATTCTGGCTTGTGTATCTACTTTGCACTTCCACTATTGTTAAT   120
121 TTATTTCACTATTTTAGGTGTGTAATATGAATTGCAAAAAATTCTTATAACAACTGCATT     180
                         M  N  C  K  K  L  L  I  T  T  A  L
181 AATATCATTAAGTACTCTATTCCAAGCATATCTTTTTCTGATACTATACAAGATGGTAA     240
     I  S  L  M  Y  S  I  P  S  I  S  F  S  D  T  I  Q  D  G  N
241 CATGGGTGGTAACTTCTATATTAGTGGAAAGTATGTACCAAGTGTCTCACATTTTGGTAG    300
     M  G  G  N  F  Y  I  S  G  K  Y  V  P  S  V  S  H  F  G  S
301 CTTCTCAGCTAAAGAAGAAAGCAAATCAACTGTTGGAGTTTTTGGATTAAAACATGATTG    360
     F  S  A  K  E  E  S  K  S  T  V  G  V  F  G  L  K  H  D  W
361 GGATGGAAGTCCAATACTTAAGAATAAACACGCTGACTTTACTGTTCCAAACTATTCGTT    420
     D  G  S  P  I  L  K  N  K  H  A  D  F  T  V  P  N  Y  S  F
421 CAGAATACGAGAACAATCCATTTCTAGGGTTTGCAGGAGCTATCGGTTACTCAATGGGTGG    480
     R  Y  E  N  N  P  F  L  G  F  A  G  A  I  G  Y  S  M  G  G
481 CCCAAGAATAGAATTCGAAATATCTTATGAAGCATTCGACGTAAAAAGTCCTAATATCAA    540
     P  R  I  E  F  E  I  S  Y  E  A  F  D  V  K  S  P  N  I  N
541 TTATCAAAATGACGCGCACACGCGCTCTATCCATCACACATCGGCAGCCATGGA        600
     Y  Q  N  D  A  H  R  Y  C  A  L  S  H  H  T  S  A  A  M  E
601 AGCTGATAAATTTGTCTTCTTAAAAAACGAAGGGTTAATTGACATATCACTTGCAATAAA    660
     A  D  K  F  V  F  L  K  N  E  G  L  I  D  I  S  L  A  I  N
661 TGCATGTTATGATATAATAAATGACAAAGTACCTGTTTCTCCTTATATATGCGCAGGTAT    720
     A  C  Y  D  I  I  N  D  K  V  P  V  S  P  Y  I  C  A  G  I
```

Fig. 1A

```
721  TGGTACTGATTTGATTTCTATGTTTGAAGCTACAAGTCCTAAAATTTCCTACCAAGGAAA  780
      G  T  D  L  I  S  M  F  E  A  T  S  P  K  I  S  Y  Q  G  K

841  CAGGATCATAGGTAATGAGTTTAGAGATATTCCTGCAATAGTACCTAGTAACTCAACTAC  900
      R  I  I  G  N  E  F  R  D  I  P  A  I  V  P  S  N  S  T  T

901  AATAAGTGGACCACAATTTGCAACAGTAACACTAAATGTGTGTCACTTTGGTTTAGAACT  960
      I  S  G  P  Q  F  A  T  V  T  L  N  V  C  H  F  G  L  E  L

961  TGGAGGAAGATTTAACTTCTAATTTTATTGTTGCCACATATTAAAAATGATCTAAACTTG  1020
      G  G  R  F  N  F  (SEQ. ID NO: 2)

1021 TTTTTAWTATTGCTACATACAAATTTATCTTCTATGCTTCCCAAGTTTTTCYCGCTATTA  1080
1081 GGGGGGGGGACCAGAAGTAATATCTCACGGAAAACTATCTCAAAATCACTAGTATTTATA  1140
1141 CTTAAACAACAGAAAACACAACTGGAGTTTTTCGAATTAAAACAAGATTGGGACGAGCAA  1200
1201 CCAATCTTATATATTCTGACTTGCTTTCTTCTGCCACTTCTACTATTTTAATTTATTGTC  1260
1261 TATATATTCTGACTTGCTTTCTTCTGCCACTTCTACTATTTTAATTTATTGTCACTAT    1320
1321 TAGGTTATAATAAWATGAATTGCMAAAGATTTTTCATAGCAAGTGCATTGATATCACTAA  1380
1381 TGTCTTTCTTACCTAGCGTATCTTTTTCTGAATCAATACATGAAGATAATAAATGGTA   1440
1441 ACTTTTACATTAGTGCAAAGTATATGCCAAGTGCCTCACACTTTGGCGTATTTCAGTTA  1500
1501 AAGAAGAGAAAAACACAACTGGAGTTTTCGGATTAAAACAAGATTGGGACGAGCAA    1560
1561 CACTAAAGGATGCAAGCWGCAGCCACACAWTAGACCCAAGTACAATG              1607

(SEQ ID NO: 1)
```

```
ECaP28      ----HTSAAME-----ADKFVELKNEGLIDISLAINACYDIINDKVPVSPYICAGIGTDLISMFEATSPKISYQGKLGISY  217
ECa28SA2                                                                                     133
ECa28SA1    HICSDGNSGDWYTAKT...L..............L.V.FML......TTE.M.F..............T.QN........LN.  227
EChP28      ----NS.ADMSSASNN................L...FML.....VVGEGI.F..........V................L..  219
OMP-1B      AI------ADK.Y.V.........ITFM..MV.T....TAEG..FI..A...V.A...NV.KDFNL.F....I..........  222
OMP-1C      ----KA.ST---NAT.SHY.L........L....ML......VVSEGI.F.........V.............IN........  218
OMP-1D      ----LLGTETQIDGAGSAS...I......L.K.FML....V.SEGI.F.........I.V...........IN..........  222
OMP-1E      ----QDNSG---IPKTS.Y.L..S.....L...FML.....ESI.L.........V...............IN..........  218
OMP-1F      -----NSGGKLSNAG..............L.....ML.....V.SEGI.F........V................N.......L.  220
MAP-1       -----DT.SSSTAG.TTS.MV...N.T....ML......ML.GM........V........V.VIN..N..L...........  219
                              VR3

ECaP28      SINPETSVFIGGHFHRIIGNEFRDIPA---IVPSNSTTISGPQF-ATVTLNVCHFGLELGGRFNF    (SEQ ID NO:2)    278
ECa28SA2                                                                                      133
ECa28SA1    T..SRV...A.......KV......KG..T---LL.DG.NIKVQQS--.......D.......I.S..F.  (SEQ ID NO:8)    287
EChP28      ..S..A...........KV......T----I.TG..LAGKGNYP.I.I.D....I.........A.    (SEQ ID NO:9)    281
OMP-1B      P.T..V.A....YY.GV..N.NK..VITPV.LEGAPQTTS----.L..IDTGY..G.V.V..T.    (SEQ ID NO:10)   283
OMP-1C      ...A....V........KVA...........ST---LKAFATPSSAATPDL.......S.........V..........      (SEQ ID NO:11)   280
OMP-1D      P..S..A..........KV..........T----MI..E.ALAGKGNYP.I...D.FY..I..............QL.....   (SEQ ID NO:12)   286
OMP-1E      .....A...........KV..........T-----LKAFVTSS--ATPDL.I....S.........................   (SEQ ID NO:13)   278
OMP-1F      ..S..A...V.......KV.............MI..T..LTGN-H..TI...S..........V..................   (SEQ ID NO:14)   280
MAP-1       .....A.I.........V......K..ATSKVFTS.GNASSAVSPGF.SAI.D..........I.I......V.........   (SEQ ID NO:15)   284
                                                    VR4
```

Fig. 3B

Eca28SA2

```
ATGAATTGTAAAAAAGTTTTCACAATAAGTGCATTGATATCATCCATATACTTCCTACCT   60
 M  N  C  K  K  V  F  T  I  S  A  L  I  S  S  I  Y  F  L  P

AATGTCTCATACTCTAACCCAGTATGTTAACAGTATGTTAATTTTTTACATATCA         120
 N  V  S  Y  S  N  P  V  Y  G  N  S  M  Y  G  N  F  Y  I  S

GGAAAGTACATGCCAAGTGTTCCTCATTTTGGAATTTTTTCAGCTGAAGAAGAGAAAAAA   180
 G  K  Y  M  P  S  V  P  H  F  G  I  F  S  A  E  E  E  K  K

AAGACAACTGTAGTATATGGCTTAAAAGAAAACTGGGCAGGAGATGCAATATCTAGTCAA   240
 K  T  T  V  V  Y  G  L  K  E  N  W  A  G  D  A  I  S  S  Q

AGTCCAGATGATAATTTTACCATTCGAAATTACTCAAGTATGCAAGCAACAAGTTT       300
 S  P  D  D  N  F  T  I  R  N  Y  S  F  K  Y  A  S  N  K  F

TTAGGGTTTGCAGTAGCTATTGGTTACTCGATAGGCAGTCCAAGAATAGAAGTTGAGATG   360
 L  G  F  A  V  A  I  G  Y  S  I  G  S  P  R  I  E  V  E  M

TCTTATGAAGCATTTGATGTGAAAAATCCAGGTGATAATTACAAAAAACGGTGCTTACAGG   420
 S  Y  E  A  F  D  V  K  N  P  G  D  N  Y  K  N  G  A  Y  R

TATTGTGCTTTATCTCATCAAGATGATGCGGATGATGACATGACTAGTGCAACTGACAAA   480
 Y  C  A  L  S  H  Q  D  D  A  D  D  D  M  T  S  A  T  D  K

TTTTGTATATTTAATTAATGAAGGATTACTTAACATATCATTTATGACAAACATATGTTAT   540
 F  V  Y  L  I  N  E  G  L  L  N  I  S  F  M  T  N  I  C  Y

GAAACAGCAAGCAAAAATATACCTCTCCTCCTTACATATGTGCAGGTATTGGTACTGAT   600
 E  T  A  S  K  N  I  P  L  S  P  Y  I  C  A  G  I  G  T  D

TTAATTCACATGTTTGAAACTACACATCCTAAAATTTCTTATCAAGGAAAGCTAGGGTTG   660
 L  I  H  M  F  E  T  T  H  P  K  I  S  Y  Q  G  K  L  G  L
```

Fig. 7A

```
GCCTACTTCGTAAGTGCAGAGTCTTCGGTTTCTTTTGGTATATATTTTCATAAAATTATA 720
 A  Y  F  V  S  A  E  S  S  V  S  F  G  I  Y  F  H  K  I  I

AATATAAGTTTAAAAATGTTCCAGCCATGGTACCTATTAACTCAGACGAGATAGTAGGA 780
 N  N  F  K  N  V  P  A  M  V  P  I  N  S  D  E  I  V  G

CCACAGTTTGCAACAGTAACATTAAATGTATGCTACTTTGGATTAGAACTGGATGTAGG 840
 P  Q  F  A  T  V  T  L  N  V  C  Y  F  G  L  E  L  G  C  R
          (SEQ ID NO: 3)
TTCAACTTCTAATTCGTGGTACACATATCACGAAGCTAAAATTGTTTTTTATCTCTGC 900
 F  N  F  *  (SEQ ID NO: 4)

TGTATACAAGAGAAAAAATAGTGAAAAATTACCTAACAATATGACAGTACAAGTTTAC 960
CAAGCTTATTCTCACAAACTTCTGTCTTTATCTCTTTACAATGAAATGTACACTT 1020
AGCTTCACTACTGTAGAGTGTGTTTATCAATGCTTTGTTTATTATACTCTACATAATAT 1080
GTTAAATTTTCTTACAAACTCACTAGTAATTTATACTAGAATATATATTCTGACTTGT 1140
                                              (SEQ ID NO: 31)

ECa28SA3
ATTTGCTTTATACTTCCACTATTGTAATTTATTTTCACTATTTTAGGTGTAATATGAAT 1200
                                                        M  N

TGCAAAAAAATTCTTATAACAACTGCATTAAATGTCATTAATGTACTATGCTCCAAGCATA 1260
 C  K  K  I  L  I  T  T  A  L  M  S  L  M  Y  Y  A  P  S  I

TCTTTTTCTGATACTATACAAGACGATAACACTGGTAGCTTCTACATCAGTGGAAAATAT 1320
 S  F  S  D  T  I  Q  D  D  N  T  G  S  F  Y  I  S  G  K  Y

GTACCAAGTGTTTCACATTTTGGTGTGTTTCTCAGCTAAAGAAGAAAGAAACTCAACTGTT 1380
 V  P  S  V  S  H  F  G  V  F  S  A  K  E  E  R  N  S  T  V

GGAGTTTTTGGATTAAAACATGATTGGAATGGAGGTACAATATCTAACTCTTCTCCAGAA 1440
 G  V  F  G  L  K  H  D  W  N  G  G  T  I  S  N  S  S  P  E
```

Fig. 7B

```
AATATATTCACAGTTCAAAATTATTCGTTAAATACGAAAAACAACCCATTCTTAGGGTTT  1500
 N  I  F  T  V  Q  N  Y  S  F  K  Y  E  N  N  P  F  L  G  F

GCAGGAGCTATTGGTTATTCAATGGGTGGCCCAAGAATAGAACTTGAAGTTCTGTACGAG  1560
 A  G  A  I  G  Y  S  M  G  G  P  R  I  E  L  E  V  L  Y  E

ACATTCGATGTGAAAAAATCAGAACAATAATTATAAGAACGGGCACACAGATACTGTGCT  1620
 T  F  D  V  K  N  Q  N  N  Y  K  N  G  A  H  R  Y  C  A

TTATCTCATCATAGTTCAGCAACAAGCATGTCCTCCGCAAGTAACAAATTTGTTTTCTTA  1680
 L  S  H  H  S  A  T  S  M  S  S  A  S  N  K  F  V  F  L

AAAAATGAAGGGTTAATTGACTTATCATTTATGATAAATGCATGCTATGACATAATAATT  1740
 K  N  E  G  L  I  D  L  S  F  M  I  N  A  C  Y  D  I  I  I

GAAGGAATGCCTTTTTCACCTTATATTGTGCAGGTGTTGGTACTGATGTTGTTTCCATG  1800
 E  G  M  P  F  S  P  Y  I  C  A  G  V  G  T  D  V  V  S  M

TTTGAAGCTATAAATCCTAAAATTTCTTACCAAGGAAAACTAGGATTAGGTTATAGTATA  1860
 F  E  A  I  N  P  K  I  S  Y  Q  G  K  L  G  L  G  Y  S  I

AGTTCAGAAGCCTCTGTTTTTATCGGTGGACACTTTCACAGAGTCATAGGTAATGAATTT  1920
 S  S  E  A  S  V  F  I  G  G  H  F  H  R  V  I  G  N  E  F

AGAGACATCCCTGCTATGGTTCCTAGTGGATCAAATCTTCCAGAAAACCAATTTGCAATA  1980
 R  D  I  P  A  M  V  P  S  G  S  N  L  P  E  N  Q  F  A  I (SEQ ID NO: 5)
GTAACACTAAATGTGTGTCACTTTGGCATAGAACTTGGAGGAAGATTTAACTTCTGA   2031
 V  T  L  N  V  C  H  F  G  I  E  L  G  G  R  F  N  F  *
                                               (SEQ ID NO: 6)
```

```
ATGAATAATAAACTCAAATTTACTATAATAAACACAGTATTAGTATGCTTATTGTCATTA  60
 M  N  N  K  L  K  F  T  I  I  N  T  V  L  V  C  L  L  S  L

CCTAATATATCTTCCTCAAAGGCCATAAACAATAACGCTAAAAAGTACTACGGATTATAT 120
 P  N  I  S  S  K  A  I  N  N  A  K  K  Y  Y  G  L  Y

ATCAGTGGACAATATAAACCCAGTGTTTCTGTTTTCAGTAATTTTTCAGTTAAAGAAACC 180
 I  S  G  Q  Y  K  P  S  V  S  V  F  S  N  F  S  V  K  E  T

AATGTCATAACTAAAAACCTTATAGCTTTAAAAAAAGATGTTGACTCTATTGAAACCAAG 240
 N  V  I  T  K  N  L  I  A  L  K  K  D  V  D  S  I  E  T  K

ACTGATGCCAGTGTAGGTATTAGTAACCCATCAAATTTTACTATCCCCTATACAGCTGTA 300
 T  D  A  S  V  G  I  S  N  P  S  N  F  T  I  P  Y  T  A  V

TTTCAAGATAATTCTGTCAATTTCAATGGAACTATTGGTTACACCTTTGCTGAAGGTACA 360
 F  Q  D  N  S  V  N  F  N  G  T  I  G  Y  T  F  A  E  G  T

AGAGTTGAAATAGAAGGTTCTTATGAGGAATTTGATGTTAAAAACCCTGGAGGCTATACA 420
 R  V  E  I  E  G  S  Y  E  E  F  D  V  K  N  P  G  G  Y  T

CTAAGTGATGCCTATCGCTATTTTGCATTAGCACGTGAAATGAAAGGTAATAGTTTTACA 480
 L  S  D  A  Y  R  Y  F  A  L  A  R  E  M  K  G  N  S  F  T

CCTAAAGAAAAAGTTTCTAATAGTATTTTTCACACTGTAATGAGAAATGATGGATTATCT 540
 P  K  E  K  V  S  N  S  I  F  H  T  V  M  R  N  D  G  L  S

ATAATATCTGTTATAGTAAATGTTTGCTACGATTTCTCTTTGAACAATTTGTCAATATCG 600
 I  I  S  V  I  V  N  V  C  Y  D  F  S  L  N  N  L  S  I  S

CCTTACATATGTGGAGGAGCAGGGGTAGATGCTATAGAATTCTTCGATGTATTACACATT 660
 P  Y  I  C  G  G  A  G  V  D  A  I  E  F  F  D  V  L  H  I

AAGTTTGCATATCAAAGCAAGCTAGGTATTGCTTATTCTCTACCATCTAACATTAGTCTC 720
 K  F  A  Y  Q  S  K  L  G  I  A  Y  S  L  P  S  N  I  S  L

TTTGCTAGTTTATATTACCATAAAGTAATGGGCAATCAATTTAAAAATTTAAATGTCCAA 780
 F  A  S  L  Y  Y  H  K  V  M  G  N  Q  F  K  N  L  N  V  Q

CATGTTGCTGAACTTGCAAGTATACCTAAAATTACATCCGCAGTTGCTACACTTAATATT 840
 H  V  A  E  L  A  S  I  P  K  I  T  S  A  V  A  T  L  N  I

GGTTATTTTGGAGGTGAAATTGGTGCAAGATTGACATTT     (SEQ ID No. 39)    879
 G  Y  F  G  G  E  I  G  A  R  L  T  F      (SEQ ID NO. 40)
```

Fig. 13

```
ATGAATTATAAGAAAATTCTAGTAAGAAGCGCGTTAATCTCATTAATGTCAATCTTACCA  60
 M  N  Y  K  K  I  L  V  R  S  A  L  I  S  L  M  S  I  L  P
TATCAGTCTTTTGCAGATCCTGTAGGTTCAAGAACTAATGATAACAAAGAAGGCTTCTAC 120
 Y  Q  S  F  A  D  P  V  G  S  R  T  N  D  N  K  E  G  F  Y
ATTAGTGCAAAGTACAATCCAAGTATATCACACTTTAGAAAATTCTCTGCTGAAGAAACT 180
 I  S  A  K  Y  N  P  S  I  S  H  F  R  K  F  S  A  E  E  T
CCTATTAATGGAACAAATTCTCTCACTAAAAAAGTTTTCGGACTAAAGAAAGATGGTGAT 240
 P  I  N  G  T  N  S  L  T  K  K  V  F  G  L  K  K  D  G  D
ATAACAAAAAAGACGATTTTACAAGAGTAGCTCCAGGCATTGATTTTCAAAATAACTTA  300
 I  T  K  K  D  D  F  T  R  V  A  P  G  I  D  F  Q  N  N  L
ATATCAGGATTTTCAGGAAGTATTGGTTACTCTATGGACGGACCAAGAATAGAACTTGAA 360
 I  S  G  F  S  G  S  I  G  Y  S  M  D  G  P  R  I  E  L  E
GCTGCATATCAACAATTTAATCCAAAAAACACCGATAACAATGATACTGATAATGGTGAA 420
 A  A  Y  Q  Q  F  N  P  K  N  T  D  N  N  D  T  D  N  G  E
TACTATAAACATTTTGCATTATCTCGTAAAGATGCAATGGAAGATCAGCAATATGTAGTA 480
 Y  Y  K  H  F  A  L  S  R  K  D  A  M  E  D  Q  Q  Y  V  V
CTTAAAAATGACGGCATAACTTTTATGTCATTGATGGTTAATACTTGCTATGACATTACA 540
 L  K  N  D  G  I  T  F  M  S  L  M  V  N  T  C  Y  D  I  T
GCTGAAGGAGTATCTTTCGTACCATATGCATGTGCAGGTATAGGAGCAGATCTTATCACT 600
 A  E  G  V  S  F  V  P  Y  A  C  A  G  I  G  A  D  L  I  T
ATTTTTAAAGACCTCAATCTAAAATTTGCTTACCAAGGAAAAATAGGTATTAGTTACCCT 660
 I  F  K  D  L  N  L  K  F  A  Y  Q  G  K  I  G  I  S  Y  P
ATCACACCAGAAGTCTCTGCATTTATTGGTGGATACTACCATGGCGTTATTGGTAATAAA 720
 I  T  P  E  V  S  A  F  I  G  G  Y  Y  H  G  V  I  G  N  K
TTTGAGAAGATACCTGTAATAACTCCTGTAGTATTAAATGATGCTCCTCAAACCACATCT 780
 F  E  K  I  P  V  I  T  P  V  V  L  N  D  A  P  Q  T  T  S
GCTTCAGTAACTCTTGACGTTGGATACTTTGGCGGAGAAATTGGAATGAGGTTCACCTTC 840
                                                  (SEQ ID No. 41)
 A  S  V  T  L  D  V  G  Y  F  G  G  E  I  G  M  R  F  T  F
                                                  (SEQ ID No. 42)
```

Fig. 14

```
ATGAACTGTAAAAAAATTCTTATAACAACTACATTGGTATCACTAACAATTCTTTTACCT 60
 M  N  C  K  K  I  L  I  T  T  T  L  V  S  L  T  I  L  L  P
GGCATATCTTTCTCCAAACCAATACATGAAAACAATACTACAGGAAACTTTTACATTATT 120
 G  I  S  F  S  K  P  I  H  E  N  N  T  T  G  N  F  Y  I  I
GGAAAATATGTACCAAGTATTTCACATTTTGGGAACTTTTCAGCTAAAGAAGAAAAAAAC 180
 G  K  Y  V  P  S  I  S  H  F  G  N  F  S  A  K  E  E  K  N
ACAACAACTGGAATTTTTGGATTAAAAGAATCATGGACTGGTGGTATCATCCTTGATAAA 240
 T  T  T  G  I  F  G  L  K  E  S  W  T  G  G  I  I  L  D  K
GAACATGCAGCTTTTAATATCCCAAATTATTCATTTAAATATGAAAATAATCCATTTTTA 300
 E  H  A  A  F  N  I  P  N  Y  S  F  K  Y  E  N  N  P  F  L
GGATTTGCAGGGGTAATTGGCTATTCAATAGGTAGTCCAAGAATAGAATTTGAAGTATCA 360
 G  F  A  G  V  I  G  Y  S  I  G  S  P  R  I  E  F  E  V  S
TACGAGACATTCGATGTACAAAATCCAGGAGATAAGTTTAACAATGATGCACATAAGTAT 420
 Y  E  T  F  D  V  Q  N  P  G  D  K  F  N  N  D  A  H  K  Y
TGTGCTTTATCCAATGATTCCAGTAAAACAATGAAAAGTGGTAAATTCGTTTTTCTCAAA 480
 C  A  L  S  N  D  S  S  K  T  M  K  S  G  K  F  V  F  L  K
AATGAAGGATTAAGTGACATATCACTCATGTTAAATGTATGTTATGATATAATAAACAAA 540
 N  E  G  L  S  D  I  S  L  M  L  N  V  C  Y  D  I  I  N  K
AGAATGCCTTTTTCACCTTACATATGTGCAGGCATTGGTACTGACTTAATATTCATGTTT 600
 R  M  P  F  S  P  Y  I  C  A  G  I  G  T  D  L  I  F  M  F
GACGCTATAAACCATAAAGCTGCTTATCAAGGAAAATTAGGTTTTAATTATCCAATAAGC 660
 D  A  I  N  H  K  A  A  Y  Q  G  K  L  G  F  N  Y  P  I  S
CCAGAAGCTAACATTTCTATGGGTGTGCACTTTCACAAAGTAACAAACAACGAGTTTAGA 720
 P  E  A  N  I  S  M  G  V  H  F  H  K  V  T  N  N  E  F  R
GTTCCTGTTCTATTAACTGCTGGAGGACTCGCTCCAGATAATCTATTTGCAATAGTAAAG 780
 V  P  V  L  L  T  A  G  G  L  A  P  D  N  L  F  A  I  V  K
TTGAGTATATGTCATTTTGGGTTAGAATTTGGGTACAGGGTCAGTTTT(SEQ ID No. 43)828
 L  S  I  C  H  F  G  L  E  F  G  Y  R  V  S  F  (SEQ ID NO. 44)
```

Fig. 15

```
ATGAATTACAAAAGATTTGTTGTAGGTGTTACGCTGAGTACATTTGTTTTTTTCTTATCT  60
 M  N  Y  K  R  F  V  V  G  V  T  L  S  T  F  V  F  F  L  S

GATGGTGCTTTTTCTGATGCAAATTTTTCTGAAGGGAGGAGAGGACTTTATATAGGTAGT 120
 D  G  A  F  S  D  A  N  F  S  E  G  R  R  G  L  Y  I  G  S

CAGTATAAAGTTGGTATTCCCAATTTTAGTAATTTTTCAGCTGAAGAAACAATTCCTGGT 180
 Q  Y  K  V  G  I  P  N  F  S  N  F  S  A  E  E  T  I  P  G

ATTACAAAAAAGATTTTTGCGTTAGGTCTTGATAAGTCTGAGATAAATACTCACAGCAAT 240
 I  T  K  K  I  F  A  L  G  L  D  K  S  E  I  N  T  H  S  N

TTTACACGATCATATGACCCTACTTATGCAAGCAGTTTTGCAGGGTTTAGTGGTATCATT 300
 F  T  R  S  Y  D  P  T  Y  A  S  S  F  A  G  F  S  G  I  I

GGATATTATGTTAATGACTTTAGGGTAGAATTTGAAGGTTCTTATGAGAATTTTGAACCT 360
 G  Y  Y  V  N  D  F  R  V  E  F  E  G  S  Y  E  N  F  E  P

GAAAGACAATGGTACCCTGAGAATAGCCAAAGCTACAAATTTTTTGCTTTGTCTCGAAAT 420
 E  R  Q  W  Y  P  E  N  S  Q  S  Y  K  F  F  A  L  S  R  N

GCTACAAATAGTGATAATAAGTTTATAGTACTAGAGAATAACGGCGTTGTTGACAAGTCT 480
 A  T  N  S  D  N  K  F  I  V  L  E  N  N  G  V  V  D  K  S

CTTAATGTAAATGTTTGTTATGATATTGCTAGTGGTAGTATTCCTTTAGCACCTTATATG 540
 L  N  V  N  V  C  Y  D  I  A  S  G  S  I  P  L  A  P  Y  M

TGTGCTGGTGTTGGTGCAGATTATATAAAGTTTTTAGGTATATCATTGCCTAAGTTTTCT 600
 C  A  G  V  G  A  D  Y  I  K  F  L  G  I  S  L  P  K  F  S

TATCAAGTTAAGTTTGGTGTCAACTACCCTCTAAATGTTAATACTATGTTGTTTGGTGGG 660
 Y  Q  V  K  F  G  V  N  Y  P  L  N  V  N  T  M  L  F  G  G

GGTTATTACCATAAGGTTGTAGGTGATAGGCATGAGAGAGTAGAAATAGCTTACCATCCT 720
 G  Y  Y  H  K  V  V  G  D  R  H  E  R  V  E  I  A  Y  H  P

ACTGCATTATCTGACGTTCCTAGAACTACTTCAGCTTCTGCTACTTTAAATACTGATTAT 780
 T  A  L  S  D  V  P  R  T  T  S  A  S  A  T  L  N  T  D  Y

TTTGGTTGGGAGATTGGATTTAGATTTGCGCTA (SEQ ID No. 45)          813
 F  G  W  E  I  G  F  R  F  A  L  (SEQ ID No. 46)
```

Fig. 16

SEQUENCE LISTING

```
<160> NUMBER OF SEQ ID NOS: 46

<210> SEQ ID NO 1
<211> LENGTH: 1607
<212> TYPE: DNA
<213> ORGANISM: Ehrlichia canis
<220> FEATURE:
<223> OTHER INFORMATION: nucleic acid sequence of E. canis p28-7

<400> SEQUENCE: 1
attttattta ttaccaatct tatataatat attaaatttc tcttacaaaa atctctaatg      60
ttttatacct aatatatata ttctggcttg tatctacttt gcacttccac tattgttaat     120
ttattttcac tattttaggt gtaatatgaa ttgcaaaaaa attcttataa caactgcatt     180
aatatcatta atgtactcta ttccaagcat atcttttttct gatactatac aagatggtaa     240
catgggtggt aacttctata ttagtggaaa gtatgtacca agtgtctcac attttggtag     300
```

```
cttctcagct aaagaagaaa gcaaatcaac tgttggagtt tttggattaa aacatgattg      360
ggatggaagt ccaatactta agaataaaca cgctgacttt actgttccaa actattcgtt      420
cagatacgag aacaatccat ttctagggtt tgcaggagct atcggttact caatgggtgg      480
cccaagaata gaattcgaaa tatcttatga agcattcgac gtaaaaagtc ctaatatcaa      540
ttatcaaaat gacgcgcaca ggtactgcgc tctatctcat cacacatcgg cagccatgga      600
agctgataaa tttgtcttct aaaaaacga agggttaatt gacatatcac ttgcaataaa       660
tgcatgttat gatataataa atgacaaagt acctgtttct ccttatatat gcgcaggtat      720
tggtactgat ttgatttcta tgtttgaagc tacaagtcct aaaatttcct accaaggaaa      780
actgggcatt agttactcta ttaatccgga aacctctgtt ttcatcggtg ggcatttcca      840
caggatcata ggtaatgagt ttagagatat tcctgcaata gtacctagta actcaactac      900
aataagtgga ccacaatttg caacagtaac actaaatgtg tgtcactttg gtttagaact      960
tggaggaaga tttaacttct aatttttattg ttgccacata ttaaaaatga tctaaacttg     1020
tttttawtat tgctacatac aaaaaaagaa aaatagtggc aaaagaatgt agcaataaga     1080 ggggggggg ggaccaaatt tatcttctat gcttcccaag ttttttcycg ctatttatga      1140
cttaaacaac agaaggtaat atcctcacgg aaaacttatc ttcaaatatt ttatttatta     1200
ccaatcttat ataatatatt aaatttctct tacaaaaatc actagtattt tataccaaaa     1260
tatatattct gacttgcttt tcttctgcac ttctactatt tttaatttat ttgtcactat     1320
taggttataa taawatgaat tgcmaaagat ttttcatagc aagtgcattg atatcactaa     1380
tgtctttctt acctagcgta tcttttttctg aatcaataca tgaagataat ataaatggta     1440
acttttacat tagtgcaaag tatatgccaa gtgcctcaca ctttggcgta ttttcagtta     1500
aagaagagaa aaacacaaca actggagttt tcggattaaa acaagattgg gacggagcaa     1560
cactaaagga tgcaagcwgc agccacacaw tagacccaag tacaatg                    1607

<210> SEQ ID NO 2
<211> LENGTH: 278
<212> TYPE: PRT
<213> ORGANISM: Ehrlichia canis
<220> FEATURE:
<223> OTHER INFORMATION: amino acid sequence of E. canis p28-7 protein

<400> SEQUENCE: 2

Met Asn Cys Lys Lys Ile Leu Ile Thr Thr Ala Leu Ile Ser Leu
                  5                  10                  15

Met Tyr Ser Ile Pro Ser Ile Ser Phe Ser Asp Thr Ile Gln Asp
                 20                  25                  30

Gly Asn Met Gly Gly Asn Phe Tyr Ile Ser Gly Lys Tyr Val Pro
                 35                  40                  45

Ser Val Ser His Phe Gly Ser Phe Ser Ala Lys Glu Glu Ser Lys
                 50                  55                  60

Ser Thr Val Gly Val Phe Gly Leu Lys His Asp trp Asp Gly Ser
                 65                  70                  75

Pro Ile Leu Lys Asn Lys His Ala Asp Phe Thr Val Pro Asn Tyr
                 80                  85                  90

Ser Phe Arg Tyr Glu Asn Asn Pro Phe Leu Gly Phe Ala Gly Ala
                 95                 100                 105

Ile Gly Tyr Ser Met Gly Gly Pro Arg Ile Glu Phe Glu Ile Ser
                110                 115                 120
```

```
Tyr Glu Ala Phe Asp Val Lys Ser Pro Asn Ile Asn Tyr Gln Asn
            125                 130                 135

Asp Ala His Arg Tyr Cys Ala Leu Ser His His Thr Ser Ala Ala
            140                 145                 150

Met Glu Ala Asp Lys Phe Val Phe Leu Lys Asn Glu Gly Leu Ile
            155                 160                 165

Asp Ile Ser Leu Ala Ile Asn Ala Cys Tyr Asp Ile Ile Asn Asp
            170                 175                 180

Lys Val Pro Val Ser Pro Tyr Ile Cys Ala Gly Ile Gly Thr Asp
            185                 190                 195

Leu Ile Ser Met Phe Glu Ala Thr Ser Pro Lys Ile Ser Tyr Gln
            200                 205                 210

Gly Lys Leu Gly Ile Ser Tyr Ser Ile Asn Pro Glu Thr Ser Val
            215                 220                 225

Phe Ile Gly Gly His Phe His Arg Ile Ile Gly Asn Glu Phe Arg
            230                 235                 240

Asp Ile Pro Ala Ile Val Pro Ser Asn Ser Thr Thr Ile Ser Gly
            245                 250                 255

Pro Gln Phe Ala Thr Val Thr Leu Asn Val Cys His Phe Gly Leu
            260                 265                 270

Glu Leu Gly Gly Arg Phe Asn Phe
            275

<210> SEQ ID NO 3
<211> LENGTH: 849
<212> TYPE: DNA
<213> ORGANISM: Ehrlichia canis
<220> FEATURE:
<221> NAME/KEY: mat_peptide
<223> OTHER INFORMATION: nucleic acid sequence of p28-5

<400> SEQUENCE: 3
atgaattgta aaaagttttt cacaataagt gcattgatat catccatata cttcctacct      60
aatgtctcat actctaaccc agtatatggt aacagtatgt atggtaattt ttacatatca     120
ggaaagtaca tgccaagtgt tcctcatttt ggaatttttt cagctgaaga agagaaaaaa     180
aagacaactg tagtatatgg cttaaaagaa aactgggcag agatgcaat atctagtcaa     240 agtccagatg ataattttac cattcgaaat tactcattca gtatgcaag caacaagttt     300 ttagggtttg cagtagctat tggttactcg ataggcagtc caagaataga agttgagatg     360
tcttatgaag catttgatgt gaaaaatcca ggtgataatt acaaaaacgg tgcttacagg     420
tattgtgctt tatctcatca agatgatgcg gatgatgaca tgactagtgc aactgacaaa     480
tttgtatatt taattaatga aggattactt aacatatcat ttatgacaaa catatgttat     540
gaaacagcaa gcaaaaatat acctctctct ccttacatat gtgcaggtat tggtactgat     600
ttaattcaca tgtttgaaac tacacatcct aaaatttctt atcaaggaaa gctagggttg     660
gcctacttcg taagtgcaga gtcttcggtt tcttttggta tatatttca taaaattata     720 aataataagt ttaaaaatgt tccagccatg gtacctatta actcagacga gatagtagga     780
ccacagtttg caacagtaac attaaatgta tgctactttg gattagaact tggatgtagg     840
ttcaacttc                                                              849

<210> SEQ ID NO 4
<211> LENGTH: 283
<212> TYPE: PRT
```

<213> ORGANISM: Ehrlichia canis
<220> FEATURE:
<223> OTHER INFORMATION: amino acid sequence of p28-5 protein

<400> SEQUENCE: 4

```

```
actgttggag tttttggatt aaaacatgat tggaatggag gtacaatatc taactcttct    240
ccagaaaata tattcacagt tcaaaattat tcgtttaaat acgaaaacaa cccattctta    300
gggtttgcag gagctattgg ttattcaatg ggtggcccaa gaatagaact tgaagttctg    360
tacgagacat tcgatgtgaa aaatcagaac aataattata agaacggcgc acacagatac    420
tgtgctttat ctcatcatag ttcagcaaca agcatgtcct ccgcaagtaa caaatttgtt    480
ttcttaaaaa atgaagggtt aattgactta tcatttatga taaatgcatg ctatgacata    540
ataattgaag gaatgccttt ttcaccttat atttgtgcag gtgttggtac tgatgttgtt    600
tccatgtttg aagctataaa tcctaaaatt tcttaccaag gaaaactagg attaggttat    660
agtataagtt cagaagcctc tgtttttatc ggtggacact ttcacagagt cataggtaat    720
gaatttagag acatccctgc tatggttcct agtggatcaa atcttccaga aaaccaattt    780
gcaatagtaa cactaaatgt gtgtcacttt ggcatagaac ttggaggaag atttaacttc    840
```

<210> SEQ ID NO 6
<211> LENGTH: 280
<212> TYPE: PRT
<213> ORGANISM: Ehrlichia canis
<220> FEATURE:
<223

```
                    230                 235                 240
Glu Phe Arg Asp Ile Pro Ala Met Val Pro Ser Gly Ser Asn Leu
                245                 250                 255

Pro Glu Asn Gln Phe Ala Ile Val Thr Leu Asn Val Cys His Phe
            260                 265                 270

Gly Ile Glu Leu Gly Gly Arg Phe Asn Phe
        275                 280

<210> SEQ ID NO 7
<211> LENGTH: 133
<212> TYPE: PRT
<213> ORGANISM: Ehrlichia canis
<220> FEATURE:
<223> OTHER INFORMATION: partial amino acid sequence of p28-5 protein

<400> SEQUENCE: 7

Met Asn Cys Lys Lys Val Phe Thr Ile Ser Ala Leu Ile Ser Ser
                  5                  10                  15

Ile Tyr Phe Leu Pro Asn Val Ser Tyr Ser Asn Pro Val Tyr Gly
             20                  25                  30

Asn Ser Met Tyr Gly Asn Phe Tyr Ile Ser Gly Lys Tyr Met Pro
         35                  40                  45

Ser Val Pro His Phe Gly Ile Phe Ser Ala Glu Glu Lys Lys
     50                  55                  60

Lys Thr Thr Val Val Tyr Gly Leu Lys Glu Asn Trp Ala Gly Asp
 65                  70                  75

Ala Ile Ser Ser Gln Ser Pro Asp Asp Asn Phe Thr Ile Arg Asn
             80                  85                  90

Tyr Ser Phe Lys Tyr Ala Ser Asn Lys Phe Leu Gly Phe Ala Val
         95                 100                 105

Ala Ile Gly Tyr Ser Ile Gly Ser Pro Arg Ile Glu Val Glu Met
     110                 115                 120

Ser Tyr Glu Ala Phe Asp Val Lys Asn Gln Gly Asn Asn
 125                 130

<210> SEQ ID NO 8
<211> LENGTH: 287
<212> TYPE: PRT
<213> ORGANISM: Ehrlichia canis
<220> FEATURE:
<223> OTHER INFORMATION: amino acid sequence of p28-4 protien

<400> SEQUENCE: 8

Met Lys Tyr Lys Lys Thr Phe Thr Val Thr Ala Leu Val Leu Leu
                  5                  10                  15

Thr Ser Phe Thr His Phe Ile Pro Phe Tyr Ser Pro Ala Arg Ala
             20                  25                  30

Ser Thr Ile His Asn Phe Tyr Ile Ser Gly Lys Tyr Met Pro Thr
         35                  40                  45

Ala Ser His Phe Gly Ile Phe Ser Ala Lys Glu Glu Gln Ser Phe
     50                  55                  60

Thr Lys Val Leu Val Gly Leu Asp Gln Arg Leu Ser His Asn Ile
 65                  70                  75

Ile Asn Asn Asn Asp Thr Ala Lys Ser Leu Lys Val Gln Asn Tyr
             80                  85                  90

Ser Phe Lys Tyr Lys Asn Asn Pro Phe Leu Gly Phe Ala Gly Ala
         95                 100                 105
```

-continued

Ile Gly Tyr Ser Ile Gly Asn Ser Arg Ile Glu Leu Glu Val Ser
            110                 115                 120

His Glu Ile Phe Asp Thr Lys Asn Pro Gly Asn Asn Tyr Leu Asn
            125                 130                 135

Asp Ser His Lys Tyr Cys Ala Leu Ser His Gly Ser His Ile Cys
            140                 145                 150

Ser Asp Gly Asn Ser Gly Asp Trp Tyr Thr Ala Lys Thr Asp Lys
            155                 160                 165

Phe Val Leu Leu Lys Asn Glu Gly Leu Leu Asp Val Ser Phe Met
            170                 175                 180

Leu Asn Ala Cys Tyr Asp Ile Thr Thr Glu Lys Met Pro Phe Ser
            185                 190                 195

Pro Tyr Ile Cys Ala Gly Ile Gly Thr Asp Leu Ile Ser Met Phe
            200                 205                 210

Glu Thr Thr Gln Asn Lys Ile Ser Tyr Gln Gly Lys Leu Gly Leu
            215                 220                 225

Asn Tyr Thr Ile Asn Ser Arg Val Ser Val Phe Ala Gly Gly His
            230                 235                 240

Phe His Lys Val Ile Gly Asn Glu Phe Lys Gly Ile Pro Thr Leu
            245                 250                 255

Leu Pro Asp Gly Ser Asn Ile Lys Val Gln Gln Ser Ala Thr Val
            260                 265                 270

Thr Leu Asp Val Cys His Phe Gly Leu Glu Ile Gly Ser Arg Phe
            275                 280                 285

Phe Phe

<210> SEQ ID NO 9
<211> LENGTH: 281
<212> TYPE: PRT
<213> ORGANISM: Ehrlichia chaffeensis
<220> FEATURE:
<223> OTHER INFORMATION: amino acid sequence of E. chaffeensis P28

<400> SEQUENCE: 9

Met Asn Tyr Lys Lys Val Phe Ile Thr Ser Ala Leu Ile Ser Leu
              5                  10                  15

Ile Ser Ser Leu Pro Gly Val Ser Phe Ser Asp Pro Ala Gly Ser
             20                  25                  30

Gly Ile Asn Gly Asn Phe Tyr Ile Ser Gly Lys Tyr Met Pro Ser
             35                  40                  45

Ala Ser His Phe Gly Val Phe Ser Ala Lys Glu Glu Arg Asn Thr
             50                  55                  60

Thr Val Gly Val Phe Gly Leu Lys Gln Asn Trp Asp Gly Ser Ala
             65                  70                  75

Ile Ser Asn Ser Ser Pro Asn Asp Val Phe Thr Val Ser Asn Tyr
             80                  85                  90

Ser Phe Lys Tyr Glu Asn Asn Pro Phe Leu Gly Phe Ala Gly Ala
             95                 100                 105

Ile Gly Tyr Ser Met Asp Gly Pro Arg Ile Glu Leu Glu Val Ser
            110                 115                 120

Tyr Glu Thr Phe Asp Val Lys Asn Gln Gly Asn Asn Tyr Lys Asn
            125                 130                 135

Glu Ala His Arg Tyr Cys Ala Leu Ser His Asn Ser Ala Ala Asp
            140                 145                 150

-continued

```
Met Ser Ser Ala Ser Asn Asn Phe Val Phe Leu Lys Asn Glu Gly
                155                 160                 165

Leu Leu Asp Ile Ser Phe Met Leu Asn Ala Cys Tyr Asp Val Val
                170                 175                 180

Gly Glu Gly Ile Pro Phe Ser Pro Tyr Ile Cys Ala Gly Ile Gly
                185                 190                 195

Thr Asp Leu Val Ser Met Phe Glu Ala Thr Asn Pro Lys Ile Ser
                200                 205                 210

Tyr Gln Gly Lys Leu Gly Leu Ser Tyr Ser Ile Ser Pro Glu Ala
                215                 220                 225

Ser Val Phe Ile Gly Gly His Phe His Lys Val Ile Gly Asn Glu
                230                 235                 240

Phe Arg Asp Ile Pro Thr Ile Ile Pro Thr Gly Ser Thr Leu Ala
                245                 250                 255

Gly Lys Gly Asn Tyr Pro Ala Ile Val Ile Leu Asp Val Cys His
                260                 265                 270

Phe Gly Ile Glu Leu Gly Gly Arg Phe Ala Phe
                275                 280

<210> SEQ ID NO 10
<211> LENGTH: 283
<212> TYPE: PRT
<213> ORGANISM: Ehrlichia chaffeensis
<220> FEATURE:
<223> OTHER INFORMATION: amino acid sequence of E. chaffeensis OMP-1B

<400> SEQUENCE: 10

Met Asn Tyr Lys Lys Ile Phe Val Ser Ser Ala Leu Ile Ser Leu
                5                   10                  15

Met Ser Ile Leu Pro Tyr Gln Ser Phe Ala Asp Pro Val Thr Ser
                20                  25                  30

Asn Asp Thr Gly Ile Asn Asp Ser Arg Glu Gly Phe Tyr Ile Ser
                35                  40                  45

Val Lys Tyr Asn Pro Ser Ile Ser His Phe Arg Lys Phe Ser Ala
                50                  55                  60

Glu Glu Ala Pro Ile Asn Gly Asn Thr Ser Ile Thr Lys Lys Val
                65                  70                  75

Phe Gly Leu Lys Lys Asp Gly Asp Ile Ala Gln Ser Ala Asn Phe
                80                  85                  90

Asn Arg Thr Asp Pro Ala Leu Glu Phe Gln Asn Asn Leu Ile Ser
                95                  100                 105

Gly Phe Ser Gly Ser Ile Gly Tyr Ala Met Asp Gly Pro Arg Ile
                110                 115                 120

Glu Leu Glu Ala Ala Tyr Gln Lys Phe Asp Ala Lys Asn Pro Asp
                125                 130                 135

Asn Asn Asp Thr Asn Ser Gly Asp Tyr Tyr Lys Tyr Phe Gly Leu
                140                 145                 150

Ser Arg Glu Asp Ala Ile Ala Asp Lys Lys Tyr Val Val Leu Lys
                155                 160                 165

Asn Glu Gly Ile Thr Phe Met Ser Leu Met Val Asn Thr Cys Tyr
                170                 175                 180

Asp Ile Thr Ala Glu Gly Val Pro Phe Ile Pro Tyr Ala Cys Ala
                185                 190                 195

Gly Val Gly Ala Asp Leu Ile Asn Val Phe Lys Asp Phe Asn Leu
                200                 205                 210
```

-continued

```
Lys Phe Ser Tyr Gln Gly Lys Ile Gly Ile Ser Tyr Pro Ile Thr
            215                 220                 225

Pro Glu Val Ser Ala Phe Ile Gly Tyr Tyr His Gly Val Ile
            230                 235                 240

Gly Asn Asn Phe Asn Lys Ile Pro Val Ile Thr Pro Val Val Leu
            245                 250                 255

Glu Gly Ala Pro Gln Thr Thr Ser Ala Leu Val Thr Ile Asp Thr
            260                 265                 270

Gly Tyr Phe Gly Gly Glu Val Gly Val Arg Phe Thr Phe
            275                 280

<210> SEQ ID NO 11
<211> LENGTH: 280
<212> TYPE: PRT
<213> ORGANISM: Ehrlichia chaffeensis
<220> FEATURE:
<223> OTHER INFORMATION: amino acid sequence of E. chaffeensis OMP-1C

<400> SEQUENCE: 11

Met Asn Cys Lys Lys Phe Phe Ile Thr Thr Ala Leu Ala Leu Pro
              5                  10                  15

Met Ser Phe Leu Pro Gly Ile Leu Leu Ser Glu Pro Val Gln Asp
             20                  25                  30

Asp Ser Val Ser Gly Asn Phe T

```
Gly Val Glu Leu Gly Gly Arg Phe Asn Phe
            275                 280
```

<210> SEQ ID NO 12
<211> LENGTH: 286
<212> TYPE: PRT
<213> ORGANISM: Ehrlichia chaffeensis
<220> FEATURE:
<223> OTHER INFORMATION: amino acid sequence of E. chaffeensis OMP-1D

<400> SEQUENCE: 12

```
Met Asn Cys Glu Lys Phe Phe Ile Thr Thr Ala Leu Thr Leu Leu
                 5                  10                  15

Met Ser Phe Leu Pro Gly Ile Ser Leu Ser Asp Pro Val Gln Asp
                20                  25                  30

Asp Asn Ile Ser Gly Asn Phe Tyr Ile Ser Gly Lys Tyr Met Pro
                35                  40                  45

Ser Ala Ser His Phe Gly Val Phe Ser Ala Lys Glu Glu Arg Asn
                50                  55                  60

Thr Thr Val Gly Val Phe Gly Ile Glu Gln Asp Trp Asp Arg Cys
                65                  70                  75

Val Ile Ser Arg Thr Thr Leu Ser Asp Ile Phe Thr Val Pro Asn
                80                  85                  90

Tyr Ser Phe Lys Tyr Glu Asn Asn Leu Phe Ser Gly Phe Ala Gly
                95                 100                 105

Ala Ile Gly Tyr Ser Met Asp Gly Pro Arg Ile Glu Leu Glu Val
               110                 115                 120

Ser Tyr Glu Ala Phe Asp Val Lys Asn Gln Gly Asn Asn Tyr Lys
               125                 130                 135

Asn Glu Ala His Arg Tyr Tyr Ala Leu Ser His Leu Leu Gly Thr
               140                 145                 150

Glu Thr Gln Ile Asp Gly Ala Gly Ser Ala Ser Val Phe Leu Ile
               155                 160                 165

Asn Glu Gly Leu Leu Asp Lys Ser Phe Met Leu Asn Ala Cys Tyr
               170                 175                 180

Asp Val Ile Ser Glu Gly Ile Pro Phe Ser Pro Tyr Ile Cys Ala
               185                 190                 195

Gly Ile Gly Ile Asp Leu Val Ser Met Phe Glu Ala Ile Asn Pro
               200                 205                 210

Lys Ile Ser Tyr Gln Gly Lys Leu Gly Leu Ser Tyr Pro Ile Ser
               215                 220                 225

Pro Glu Ala Ser Val Phe Ile Gly Gly His Phe His Lys Val Ile
               230                 235                 240

Gly Asn Glu Phe Arg Asp Ile Pro Thr Met Ile Pro Ser Glu Ser
               245                 250                 255

Ala Leu Ala Gly Lys Gly Asn Tyr Pro Ala Ile Val Thr Leu Asp
               260                 265                 270

Val Phe Tyr Phe Gly Ile Glu Leu Gly Gly Arg Phe Asn Phe Gln
               275                 280                 285

Leu
```

<210> SEQ ID NO 13
<211> LENGTH: 278
<212> TYPE: PRT
<213> ORGANISM: Ehrlichia chaffeensis
<220> FEATURE:
<223> OTHER INFORMATION: amino acid sequence of E. chaffeensis OMP-1E -continued

```
<400> SEQUENCE: 13

Met Asn Cys Lys Lys Phe Phe Ile Thr Thr Ala Leu Val Ser Leu
                 5                  10                  15

Met Ser Phe Leu Pro Gly Ile Ser Phe Ser Asp Pro Val Gln Gly
                20                  25                  30

Asp Asn Ile Ser Gly Asn Phe Tyr Val Ser Gly Lys Tyr Met Pro
                35                  40                  45

Ser Ala Ser His Phe Gly Met Phe Ser Ala Lys Glu Glu Lys Asn
                50                  55                  60

Pro Thr Val Ala Leu Tyr Gly Leu Lys Gln Asp Trp Glu Gly Ile
                65                  70                  75

Ser Ser Ser Ser His Asn Asp Asn His Phe Asn Asn Lys Gly Tyr
                80                  85                  90

Ser Phe Lys Tyr Glu Asn Asn Pro Phe Leu Gly Phe Ala Gly Ala
                95                 100                 105

Ile Gly Tyr Ser Met Gly Gly Pro Arg Val Glu Phe Glu Val Ser
               110                 115                 120

Tyr Glu Thr Phe Asp Val Lys Asn Gln Gly Asn Asn Tyr Lys Asn
               125                 130                 135

Asp Ala His Arg Tyr Cys Ala Leu Gly Gln Gln Asp Asn Ser Gly
               140                 145                 150

Ile Pro Lys Thr Ser Lys Tyr Val Leu Leu Lys Ser Glu Gly Leu
               155                 160                 165

Leu Asp Ile Ser Phe Met Leu Asn Ala Cys Tyr Asp Ile Ile Asn
               170                 175                 180

Glu Ser Ile Pro Leu Ser Pro Tyr Ile Cys Ala Gly Val Gly Thr
               185                 190                 195

Asp Leu Ile Ser Met Phe Glu Ala Thr Asn Pro Lys Ile Ser Tyr
               200                 205                 210

Gln Gly Lys Leu Gly Leu Ser Tyr Ser Ile Asn Pro Glu Ala Ser
               215                 220                 225

Val Phe Ile Gly Gly His Phe His Lys Val Ile Gly Asn Glu Phe
               230                 235                 240

Arg Asp Ile Pro Thr Leu Lys Ala Phe Val Thr Ser Ser Ala Thr
               245                 250                 255

Pro Asp Leu Ala Ile Val Thr Leu Ser Val Cys His Phe Gly Ile
               260                 265                 270

Glu Leu Gly Gly Arg Phe Asn Phe
               275

<210> SEQ ID NO 14
<211> LENGTH: 280
<212> TYPE: PRT
<213> ORGANISM: Ehrlichia chaffeensis
<220> FEATURE:
<223> OTHER INFORMATION: amino acid sequence of E. chaffeensis OMP-1F

<400> SEQUENCE: 14

Met Asn Cys Lys Lys Phe Phe Ile Thr Thr Thr Leu Val Ser Leu
                 5                  10                  15

Met Ser Phe Leu Pro Gly Ile Ser Phe Ser Asp Ala Val Gln Asn
                20                  25                  30

Asp Asn Val Gly Gly Asn Phe Tyr Ile Ser Gly Lys Tyr Val Pro
                35                  40                  45
```

```
Ser Val Ser His Phe Gly Val Phe Ser Ala Lys Gln Glu Arg Asn
             50                  55                  60

Thr Thr Thr Gly Val Phe Gly Leu Lys Gln Asp Trp Asp Gly Ser
             65                  70                  75

Thr Ile Ser Lys Asn Ser Pro Glu Asn Thr Phe Asn Val Pro Asn
             80                  85                  90

Tyr Ser Phe Lys Tyr Glu Asn Asn Pro Phe Leu Gly Phe Ala Gly
             95                 100                 105

Ala Val Gly Tyr Leu Met Asn Gly Pro Arg Ile Glu Leu Glu Met
            110                 115                 120

Ser Tyr Glu Thr Phe Asp Val Lys Asn Gln Gly Asn Asn Tyr Lys
            125                 130                 135

Asn Asp Ala His Lys Tyr Tyr Ala Leu Thr His Asn Ser Gly Gly
            140                 145                 150

Lys Leu Ser Asn Ala Gly Asp Lys Phe Val Phe Leu Lys Asn Glu
            155                 160                 165

Gly Leu Leu Asp Ile Ser Leu Met Leu Asn Ala Cys Tyr Asp Val
            170                 175                 180

Ile Ser Glu Gly Ile Pro Phe Ser Pro Tyr Ile Cys Ala Gly Val
            185                 190                 195

Gly Thr Asp Leu Ile Ser Met Phe Glu Ala Ile Asn Pro Lys Ile
            200                 205                 210

Ser Tyr Gln Gly Lys Leu Gly Leu Ser Tyr Ser Ile Ser Pro Glu
            215                 220                 225

Ala Ser Val Phe Val Gly Gly His Phe His Lys Val Ile Gly Asn
            230                 235                 240

Glu Phe Arg Asp Ile Pro Ala Met Ile Pro Ser Thr Ser Thr Leu
            245                 250                 255

Thr Gly Asn His Phe Thr Ile Val Thr Leu Ser Val Cys His Phe
            260                 265                 270

Gly Val Glu Leu Gly Gly Arg Phe Asn Phe
            275                 280

<210> SEQ ID NO 15
<211> LENGTH: 284
<212> TYPE: PRT
<213> ORGANISM: Cowdria ruminantium
<220> FEATURE:
<223> OTHER INFORMATION: amino acid sequence of C. ruminantium MAP-1

<400> SEQUENCE: 15

Met Asn Cys Lys Lys Ile Phe Ile Thr Ser Thr Leu Ile Ser Leu
              5                  10                  15

Val Ser Phe Leu Pro Gly Val Ser Phe Ser Asp Val Ile Gln Glu
             20                  25                  30

Glu Asn Asn Pro Val Gly Ser Val Tyr Ile Ser Ala Lys Tyr Met
             35                  40                  45

Pro Thr Ala Ser His Phe Gly Lys Met Ser Ile Lys Glu Asp Ser
             50                  55                  60

Arg Asp Thr Lys Ala Val Phe Gly Leu Lys Lys Asp Trp Asp Gly
             65                  70                  75

Val Lys Thr Pro Ser Gly Asn Thr Asn Ser Ile Phe Thr Glu Lys
             80                  85                  90

Asp Tyr Ser Phe Lys Tyr Glu Asn Asn Pro Phe Leu Gly Phe Ala
             95                 100                 105
```

```
Gly Ala Val Gly Tyr Ser Met Asn Gly Pro Arg Ile Glu Phe Glu
            110                 115                 120

Val Ser Tyr Glu Thr Phe Asp Val Arg Asn Pro Gly Gly Asn Tyr
            125                 130                 135

Lys Asn Asp Ala His Met Tyr Cys Ala Leu Asp Thr Ala Ser Ser
            140                 145                 150

Ser Thr Ala Gly Ala Thr Thr Ser Val Met Val Lys Asn Glu Asn
            155                 160                 165

Leu Thr Asp Ile Ser Leu Met Leu Asn Ala Cys Tyr Asp Ile Met
            170                 175                 180

Leu Asp Gly Met Pro Val Ser Pro Tyr Val Cys Ala Gly Ile Gly
            185                 190                 195

Thr Asp Leu Val Ser Val Ile Asn Ala Thr Asn Pro Lys Leu Ser
            200                 205                 210

Tyr Gln Gly Lys Leu Gly Ile Ser Tyr Ser Ile Asn Pro Glu Ala
            215                 220                 225

Ser Ile Phe Ile Gly Gly His Phe His Arg Val Ile Gly Asn Glu
            230                 235                 240

Phe Lys Asp Ile Ala Thr Ser Lys Val Phe Thr Ser Ser Gly Asn
            245                 250                 255

Ala Ser Ser Ala Val Ser Pro Gly Phe Ala Ser Ala Ile Leu Asp
            260                 265                 270

Val Cys His Phe Gly Ile Glu Ile Gly Gly Arg Phe Val Phe
            275                 280
```

<210> SEQ ID NO 16
<211> LENGTH: 20
<212> TYPE: DNA
<213> ORGANISM: artificial sequence
<220> FEATURE:
<221> NAME/KEY: primer_bind
<222> LOCATION: nucleotides 313-332 of C. ruminantium MAP-1,
<223> OTHER INFORMATION: forward primer 793 for PCR

<400> SEQUENCE: 16
gcaggagctg ttggttactc                                          20

<210> SEQ ID NO 17
<211> LENGTH: 21
<212> TYPE: DNA
<213> ORGANISM: artificial sequence
<220> FEATURE:
<221> NAME/KEY: primer_bind
<222> LOCATION: nucleotides 823-843 of C. ruminantium MAP-1,
<223> OTHER INFORMATION: reverse primer 1330 for PCR

<400> SEQUENCE: 17
ccttcctcca agttctatgc c                                        21

<210> SEQ ID NO 18
<211> LENGTH: 24
<212> TYPE: DNA
<213> ORGANISM: artificial sequence
<220> FEATURE:
<221> NAME/KEY: primer_bind
<223> OTHER INFORMATION: primer 46f, specific for p28-5 gene

<400> SEQUENCE: 18
atatacttcc tacctaatgt ctca                                     24

<210> SEQ ID NO 19

```
<211> LENGTH: 20
<212> TYPE: DNA
<213> ORGANISM: artificial sequence
<220> FEATURE:
<221> NAME/KEY: primer_bind
<223> OTHER INFORMATION: primer used for sequencing 28-kDa protein
      genes in E. canis

<400> SEQUENCE: 19
agtgcagagt cttcggtttc                                               20

<210> SEQ ID NO 20
<211> LENGTH: 18
<212> TYPE: DNA
<213> ORGANISM: artificial sequence
<220> FEATURE:
<221> NAME/KEY: primer_bind
<223> OTHER INFORMATION: primer used for sequencing 28-kDa protein
      genes in E. canis

<400> SEQUENCE: 20
gttacttgcg gaggacat                                                 18

<210> SEQ ID NO 21
<211> LENGTH: 24
<212> TYPE: DNA
<213> ORGANISM: artificial sequence
<220> FEATURE:
<221> NAME/KEY: primer_bind
<222> LOCATION: nucleotides 687-710 of E. canis p28-7
<223> OTHER INFORMATION: primer 394 for PCR

<400> SEQUENCE: 21
gcatttccac aggatcatag gtaa                                          24

<210> SEQ ID NO 22
<211> LENGTH: 24
<212> TYPE: DNA
<213> ORGANISM: artificial sequence
<220> FEATURE:
<221> NAME/KEY: primer_bind
<222> LOCATION: nucleotides 710-687 of E. canis p28-7
<223> OTHER INFORMATION: primer 394C for PCR

<400> SEQUENCE: 22
ttacctatga tcctgtggaa atgc                                          24

<210> SEQ ID NO 23
<211> LENGTH: 20
<212> TYPE: DNA
<213> ORGANISM: artificial sequence
<220> FEATURE:
<221> NAME/KEY: primer_bind
<223> OTHER INFORMATION: primer 793C which anneals to a region with
      E. canis p28-7, used to amplify the intergenic region between
      gene p28-6 and p28-7

<400> SEQUENCE: 23
gagtaaccaa cagctcctgc                                               20

<210> SEQ ID NO 24
<211> LENGTH: 24
<212> TYPE: DNA
<213> ORGANISM: artificial sequence
<220> FEATURE:
<221> NAME/KEY: primer_bind
<222> LOCATION:
<223> OTHER INFORMATION: primer EC28OM-F complementary to noncoding
      regions adjacent to the open reading frame of p28-7
```

```
<400> SEQUENCE: 24
tctactttgc acttccacta ttgt                                          24

<210> SEQ ID NO 25
<211> LENGTH: 24
<212> TYPE: DNA
<213> ORGANISM: artificial sequence
<220> FEATURE:
<221> NAME/KEY: primer_bind
<222> LOCATION:
<223> OTHER INFORMATION: primer EC28OM-R complementary to noncoding
      regions adjacent to the open reading frame of p28-7

<400> SEQUENCE: 25
attcttttgc cactattttt cttt                                          24

<210> SEQ ID NO 26
<211> LENGTH: 25
<212> TYPE: DNA
<213> ORGANISM: artificial sequence
<220> FEATURE:
<221> NAME/KEY: primer_bind
<223> OTHER INFORMATION: primer ECaSA3-2 corresponding to regions within
      p28-6, used to amplify the intergenic region NC3
      between gene p28-6 and p28-7

<400> SEQUENCE: 26
ctaggattag gttatagtat aagtt                                         25

<210> SEQ ID NO 27
<211> LENGTH: 23
<212> TYPE: PRT
<213> ORGANISM: Ehrlichia canis
<220> FEATURE:
<221> NAME/KEY: PEPTIDE
<223> OTHER INFORMATION: a predicted N-terminal signal peptide of p28-7
      and p28-6

<400> SEQUENCE: 27

Met Asn Cys Lys Lys Ile Leu Ile Thr Thr Ala Leu Met Ser Leu
                 5                  10                  15

Met Tyr Tyr Ala Pro Ser Ile Ser
                20

<210> SEQ ID NO 28
<211> LENGTH: 25
<212> TYPE: PRT
<213> ORGANISM: Ehrlichia chaffeensis
<220> FEATURE:
<223> OTHER INFORMATION: amino acid sequence of N-terminal signal
      peptide of E. chaffeensis P28

<400> SEQUENCE: 28

Met Asn Tyr Lys Lys Ile Leu Ile Thr Ser Ala Leu Ile Ser Leu
                 5                  10                  15

Ile Ser Ser Leu Pro Gly Val Ser Phe Ser
                20                  25

<210> SEQ ID NO 29
<211> LENGTH: 26
<212> TYPE: PRT
<213> ORGANISM: Ehrlichia canis
<220> FEATURE:
<223> OTHER INFORMATION: amino acid sequence of putative cleavage site of
      p28-7
```

```
<400> SEQUENCE: 29

Met Asn Cys Lys Lys Ile Leu Ile Thr Thr Ala Leu Ile Ser Leu
                5                  10                  15

Met Tyr Ser Ile Pro Ser Ile Ser Ser Phe Ser
                20                  25

<210> SEQ ID NO 30
<211> LENGTH: 299
<212> TYPE: DNA
<213> ORGANISM: Ehrlichia canis
<220> FEATURE:
<223> OTHER INFORMATION: nucleic acid sequence of intergenic noncoding
      region 1 (28NC1)

<400> SEQUENCE: 30
taatacttct attgtacatg ttaaaaatag tactagtttg cttctgtggt ttataaacgc      60
aagagagaaa tagttagtaa taattagaa agtaaatat tagaaaagtc atatgttttt     120
cattgtcatt gatactcaac taaaagtagt ataaatgtta cttattaata attttacgta    180
gtatattaaa tttcccttac aaaagccact agtatttat actaaaagct atactttggc     240
ttgtatttaa tttgtatttt tactactgtt aattactttt cactgtttct ggtgtaaat     299

<210> SEQ ID NO 31
<211> LENGTH: 345
<212> TYPE: DNA
<213> ORGANISM: Ehrlichia canis
<220> FEATURE:
<223> OTHER INFORMATION: nucleic acid sequence of intergenic noncoding
      region 2 (28NC2)

<400> SEQUENCE: 31
taatttcgtg gtacacatat cacgaagcta aaattgtttt tttatctctg ctgtatacaa      60
gagaaaaaat agtagtgaaa attacctaac aatatgacag tacaagttta ccaagcttat    120
tctcacaaaa cttcttgtgt cttttatctc tttacaatga aatgtacact agcttcact    180 actgtagagt gtgttatca atgctttgtt tattaatact ctacataata tgttaaattt     240
ttcttacaaa actcactagt aatttatact agaatatata ttctgacttg tatttgcttt    300
atacttccac tattgttaat ttattttcac tattttaggt gtaat                   345

<210> SEQ ID NO 32
<211> LENGTH: 345
<212> TYPE: DNA
<213> ORGANISM: Ehrlichia canis
<220> FEATURE:
<223> OTHER INFORMATION: nucleic acid sequence of intergenic noncoding
      region 3 (28NC3)

<400> SEQUENCE: 32
tgattttatt gttgccacat attaaaaatg atctaaactt gttttttatta ttgctacata    60 caaaaaaaag aaaaatagtg gcaaaagaat gtagcaataa gagggggggg ggggactaaa   120
tttaccttct attcttctaa tattctttac tatattcaaa tagcacaact caatgcttcc   180
aggaaaatat gttctaata ttttatttat taccaatcct tatataatat attaaatttc    240
tcttacaaaa atctctaatg ttttatactt aatatatata ttctggcttg tatttacttt    300
gcacttccac tattgttaat ttattttcac tattttaggt gtaat                   345

<210> SEQ ID NO 33
<211> LENGTH: 355
<212> TYPE: DNA
```

```
<213> ORGANISM: Ehrlichia canis
<220> FEATURE:
<223> OTHER INFORMATION: nucleic acid sequence of intergenic noncoding
      region 4 (28NC4)

<400> SEQUENCE: 33 taatttttatt gttgccacat attaaaaatg atctaaactt gttttttawta ttgctacata      60 caaaaaaaga aaatagtgg caaagaatg tagcaataag agggggggg gggaccaaat         120 ttatcttcta tgcttcccaa gttttttcyc gctatttatg acttaaacaa cagaaggtaa     180
tatcctcacg gaaaacttat cttcaaatat tttatttatt accaatctta tataatatat     240
taaatttctc ttacaaaaat cactagtatt ttataccaaa atatatattc tgacttgctt     300
ttcttctgca cttctactat ttttaattta tttgtcacta ttaggttata ataaw           355

<210> SEQ ID NO 34
<211> LENGTH: 24
<212> TYPE: DNA
<213> ORGANISM: artificial sequence
<220> FEATURE:
<223> OTHER INFORMATION: primer p28-5-818f

<400> SEQUENCE: 34
ttaaacatat gccacttcgg acta                                              24

<210> SEQ ID NO 35
<211> LENGTH: 28
<212> TYPE: DNA
<213> ORGANISM: artificial sequence
<220> FEATURE:
<223> OTHER INFORMATION: primer 1191

<400> SEQUENCE: 35
tatgatcgtg taaaattgct gtgagtat                                          28

<210> SEQ ID NO 36
<211> LENGTH: 20
<212> TYPE: DNA
<213> ORGANISM: artificial sequence
<220> FEATURE:
<223> OTHER INFORMATION: primer ECa28-75C

<400> SEQUENCE: 36
tactggcacg tgctggacta                                                   20

<210> SEQ ID NO 37
<211> LENGTH: 22
<212> TYPE: DNA
<213> ORGANISM: artificial sequence
<220> FEATURE:
<223> OTHER INFORMATION: primer ECa5'-1600

<400> SEQUENCE: 37
caccaataaa tgcagagact tc                                                22

<210> SEQ ID NO 38
<211> LENGTH: 26
<212> TYPE: DNA
<213> ORGANISM: artificial sequence
<220> FEATURE:
<223> OTHER INFORMATION: primer 3125

<400> SEQUENCE: 38
aatccatcat ttctcattac agtgtg                                            26
```

-continued

<210> SEQ ID NO 39
<211> LENGTH: 879
<212> TYPE: DNA
<213> ORGANISM: Ehrlichia canis
<220> FEATURE:
<223> OTHER INFORMATION: nucleic acid sequence of E. canis p28-1

<400> SEQUENCE: 39

| | | |
|---|---|---|
| atgaataata aactcaaatt tactataata aacacagtat tagtatgctt attgtcatta | 60 |
| cctaatatat cttcctcaaa ggccataaac aataacgcta aaaagtacta cggattatat | 120 |
| atcagtggac aatataaacc cagtgtttct gttttcagta attttttcagt taaagaaacc | 180 |
| aatgtcataa ctaaaaacct tatagcttta aaaaaagatg ttgactctat tgaaaccaag | 240 |
| actgatgcca gtgtaggtat tagtaaccca tcaaatttta ctatcccta tacagctgta | 300 |
| tttcaagata attctgtcaa tttcaatgga actattggtt acacctttgc tgaaggtaca | 360 |
| agagttgaaa tagaaggttc ttatgaggaa tttgatgtta aaaaccctgg aggctataca | 420 |
| ctaagtgatg cctatcgcta ttttgcatta gcacgtgaaa tgaaggtaa tagttttaca | 480 |
| cctaaagaaa aagtttctaa tagtattttt cacactgtaa tgagaaatga tggattatct | 540 |
| ataatatctg ttatagtaaa tgtttgctac gatttctctt tgaacaattt gtcaatatcg | 600 |
| ccttacatat gtggaggagc aggggtagat gctatagaat cttcgatgt attacacatt | 660 |
| aagtttgcat atcaaagcaa gctaggtatt gcttattctc taccatctaa cattagtctc | 720 |
| tttgctagtt tatattacca taaagtaatg ggcaatcaat ttaaaaattt aaatgtccaa | 780 |
| catgttgctg aacttgcaag tatacctaaa attacatccg cagttgctac acttaatatt | 840 |
| ggttattttg gaggtgaaat tggtgcaaga ttgacattt | 879 |

<210> SEQ ID NO 40
<211> LENGTH: 293
<212> TYPE: PRT
<213> ORGANISM: Ehrlichia canis
<220> FEATURE:
<223> OTHER INFORMATION: amino acid sequence of E. canis p28-1 protein

<400> SEQUENCE: 40

```
Met Asn Asn Lys Leu Lys Phe Thr Ile Ile Asn Thr Val Leu Val
              5                   10                  15

Cys Leu Leu Ser Leu Pro Asn Ile Ser Ser Lys Ala Ile Asn
             20                  25                  30

Asn Asn Ala Lys Lys Tyr Tyr Gly Leu Tyr Ile Ser Gly Gln Tyr
             35                  40                  45

Lys Pro Ser Val Ser Val Phe Ser Asn Phe Ser Val Lys Glu Thr
             50                  55                  60

Asn Val Ile Thr Lys Asn Leu Ile Ala Leu Lys Lys Asp Val Asp
             65                  70                  75

Ser Ile Glu Thr Lys Thr Asp Ala Ser Val Gly Ile Ser Asn Pro
             80                  85                  90

Ser Asn Phe Thr Ile Pro Tyr Thr Ala Val Phe Gln Asp Asn Ser
             95                 100                 105

Val Asn Phe Asn Gly Thr Ile Gly Tyr Thr Phe Ala Glu Gly Thr
            110                 115                 120

Arg Val Glu Ile Glu Gly Ser Tyr Glu Glu Phe Asp Val Lys Asn
            125                 130                 135

Pro Gly Gly Tyr Thr Leu Ser Asp Ala Tyr Arg Tyr Phe Ala Leu
            140                 145                 150
```

```
Ala Arg Glu Met Lys Gly Asn Ser Phe Thr Pro Lys Glu Lys Val
            155                 160                 165

Ser Asn Ser Ile Phe His Thr Val Met Arg Asn Asp Gly Leu Ser
            170                 175                 180

Ile Ile Ser Val Ile Val Asn Val Cys Tyr Asp Phe Ser Leu Asn
            185                 190                 195

Asn Leu Ser Ile Ser Pro Tyr Ile Cys Gly Gly Ala Gly Val Asp
            200                 205                 210

Ala Ile Glu Phe Phe Asp Val Leu His Ile Lys Phe Ala Tyr Gln
            215                 220                 225

Ser Lys Leu Gly Ile Ala Tyr Ser Leu Pro Ser Asn Ile Ser Leu
            230                 235                 240

Phe Ala Ser Leu Tyr Tyr His Lys Val Met Gly Asn Gln Phe Lys
            245                 250                 255

Asn Leu Asn Val Gln His Val Ala Glu Leu Ala Ser Ile Pro Lys
            260                 265                 270

Ile Thr Ser Ala Val Ala Thr Leu Asn Ile Gly Tyr Phe Gly Gly
            275                 280                 285

Glu Ile Gly Ala Arg Leu Thr Phe
            290             293

<210> SEQ ID NO 41
<211> LENGTH: 840
<212> TYPE: DNA
<213> ORGANISM: Ehrlichia canis
<220> FEATURE:
<223> OTHER INFORMATION: nucleic acid sequence of E. canis p28-2

<400> SEQUENCE: 41
atgaattata agaaaattct agtaagaagc gcgttaatct cattaatgtc aatcttacca    60
tatcagtctt ttgcagatcc tgtaggttca agaactaatg ataacaaaga aggcttctac   120
attagtgcaa agtacaatcc aagtatatca cactttagaa aattctctgc tgaagaaact   180
cctattaatg gaacaaattc tctcactaaa aaagttttcg gactaaagaa agatggtgat   240
ataacaaaaa aagacgattt tacaagagta gctccaggca ttgattttca aaataactta   300
atatcaggat tttcaggaag tattggttac tctatggacg gaccaagaat agaacttgaa   360
gctgcatatc aacaatttaa tccaaaaaac accgataaca atgatactga taatggtgaa   420
tactataaac attttgcatt atctcgtaaa gatgcaatgg aagatcagca atatgtagta   480
cttaaaaatg acggcataac ttttatgtca ttgatggtta atacttgcta tgacattaca   540
gctgaaggag tatctttcgt accatatgca tgtgcaggta taggagcaga tcttatcact   600 attttaaag acctcaatct aaaatttgct taccaaggaa aaataggtat tagttaccct   660
atcacaccag aagtctctgc atttattggt ggatactacc atggcgttat tggtaataaa   720
tttgagaaga tacctgtaat aactcctgta gtattaaatg atgctcctca aaccacatct   780
gcttcagtaa ctcttgacgt tggatacttt ggcggagaaa ttggaatgag gttcaccttc   840

<210> SEQ ID NO 42
<211> LENGTH: 280
<212> TYPE: PRT
<213> ORGANISM: Ehrlichia canis
<220> FEATURE:
<223> OTHER INFORMATION: amino acid sequence of E. canis p28-2 protein

<400> SEQUENCE: 42
```

-continued

Met Asn Tyr Lys Lys Ile Leu Val Arg Ser Ala Leu Ile Ser Leu
            5                   10                  15

Met Ser Ile Leu Pro Tyr Gln Ser Phe Ala Asp Pro Val Gly Ser
            20                  25                  30

Arg Thr Asn Asp Asn Lys Glu Gly Phe Tyr Ile Ser Ala Lys Tyr
            35                  40                  45

Asn Pro Ser Ile Ser His Phe Arg Lys Phe Ser Ala Glu Glu Thr
            50                  55                  60

Pro Ile Asn Gly Thr Asn Ser Leu Thr Lys Lys Val Phe Gly Leu
            65                  70                  75

Lys Lys Asp Gly Asp Ile Thr Lys Lys Asp Asp Phe Thr Arg Val
            80                  85                  90

Ala Pro Gly Ile Asp Phe Gln Asn Asn Leu Ile Ser Gly Phe Ser
            95                  100                 105

Gly Ser Ile Gly Tyr Ser Met Asp Gly Pro Arg Ile Glu Leu Glu
            110                 115                 120

Ala Ala Tyr Gln Gln Phe Asn Pro Lys Asn Thr Asp Asn Asn Asp
            125                 130                 135

Thr Asp Asn Gly Glu Tyr Tyr Lys His Phe Ala Leu Ser Arg Lys
            140                 145                 150

Asp Ala Met Glu Asp Gln Gln Tyr Val Val Leu Lys Asn Asp Gly
            155                 160                 165

Ile Thr Phe Met Ser Leu Met Val Asn Thr Cys Tyr Asp Ile Thr
            170                 175                 180

Ala Glu Gly Val Ser Phe Val Pro Tyr Ala Cys Ala Gly Ile Gly
            185                 190                 195

Ala Asp Leu Ile Thr Ile Phe Lys Asp Leu Asn Leu Lys Phe Ala
            200                 205                 210

Tyr Gln Gly Lys Ile Gly Ile Ser Tyr Pro Ile Thr Pro Glu Val
            215                 220                 225

Ser Ala Phe Ile Gly Gly Tyr Tyr His Gly Val Ile Gly Asn Lys
            230                 235                 240

Phe Glu Lys Ile Pro Val Ile Thr Pro Val Val Leu Asn Asp Ala
            245                 250                 255

Pro Gln Thr Thr Ser Ala Ser Val Thr Leu Asp Val Gly Tyr Phe
            260                 265                 270

Gly Gly Glu Ile Gly Met Arg Phe Thr Phe
            275                 280

<210> SEQ ID NO 43
<211> LENGTH: 828
<212> TYPE: DNA
<213> ORGANISM: Ehrlichia canis
<220> FEATURE:
<223> OTHER INFORMATION: nucleic acid sequence of E. canis p28-3

<400> SEQUENCE: 43
atgaactgta aaaaaattct tataacaact acattggtat cactaacaat tcttttacct      60
ggcatatctt tctccaaacc aatacatgaa acaatacta caggaaactt ttacattatt      120
ggaaaatatg taccaagtat ttcacatttt gggacttttt cagctaaaga agaaaaaaac      180
acaacaactg gaattttttgg attaaaagaa tcatggactg tggtatcat ccttgataaa      240 gaacatgcag cttttaatat cccaaattat tcatttaaat atgaaaataa tccatttta      300 ggatttgcag gggtaattgg ctattcaata ggtagtccaa gaatagaatt tgaagtatca      360

```
tacgagacat tcgatgtaca aaatccagga gataagttta acaatgatgc acataagtat      420
tgtgctttat ccaatgattc cagtaaaaca atgaaaagtg gtaaattcgt ttttctcaaa      480
aatgaaggat taagtgacat atcactcatg ttaaatgtat gttatgatat aataaacaaa      540
agaatgcctt tttcacctta catatgtgca ggcattggta ctgacttaat attcatgttt      600
gacgctataa accataaagc tgcttatcaa ggaaaattag gttttaatta tccaataagc      660
ccagaagcta acatttctat gggtgtgcac tttcacaaag taacaaacaa cgagtttaga      720
gttcctgttc tattaactgc tggaggactc gctccagata atctatttgc aatagtaaag      780
ttgagtatat gtcattttgg gttagaattt gggtacaggg tcagtttt                   828
```

<210> SEQ ID NO 44
<211> LENGTH: 276
<212> TYPE: PRT
<213> ORGANISM: Ehrlichia canis
<220> FEATURE:
<223> OTHER INFORMATION: amino acid sequence of E. canis p28-3 protein

<400> SEQUENCE: 44

```
Met Asn Cys Lys Lys Ile Leu Ile Thr Thr Thr Leu Val Ser Leu
                5                   10                  15

Thr Ile Leu Leu Pro Gly Ile Ser Phe Ser Lys Pro Ile His Glu
                20                  25                  30

Asn Asn Thr Thr Gly Asn Phe Tyr Ile Ile Gly Lys Tyr Val Pro
                35                  40                  45

Ser Ile Ser His Phe Gly Asn Phe Ser Ala Lys Glu Glu Lys Asn
                50                  55                  60

Thr Thr Thr Gly Ile Phe Gly Leu Lys Glu Ser Trp Thr Gly Gly
                65                  70                  75

Ile Ile Leu Asp Lys Glu His Ala Ala Phe Asn Ile Pro Asn Tyr
                80                  85                  90

Ser Phe Lys Tyr Glu Asn Asn Pro Phe Leu Gly Phe Ala Gly Val
                95                  100                 105

Ile Gly Tyr Ser Ile Gly Ser Pro Arg Ile Glu Phe Glu Val Ser
                110                 115                 120

Tyr Glu Thr Phe Asp Val Gln Asn Pro Gly Asp Lys Phe Asn Asn
                125                 130                 135

Asp Ala His Lys Tyr Cys Ala Leu Ser Asn Asp Ser Ser Lys Thr
                140                 145                 150

Met Lys Ser Gly Lys Phe Val Phe Leu Lys Asn Glu Gly Leu Ser
                155                 160                 165

Asp Ile Ser Leu Met Leu Asn Val Cys Tyr Asp Ile Ile Asn Lys
                170                 175                 180

Arg Met Pro Phe Ser Pro Tyr Ile Cys Ala Gly Ile Gly Thr Asp
                185                 190                 195

Leu Ile Phe Met Phe Asp Ala Ile Asn His Lys Ala Ala Tyr Gln
                200                 205                 210

Gly Lys Leu Gly Phe Asn Tyr Pro Ile Ser Pro Glu Ala Asn Ile
                215                 220                 225

Ser Met Gly Val His Phe His Lys Val Thr Asn Asn Glu Phe Arg
                230                 235                 240

Val Pro Val Leu Leu Thr Ala Gly Gly Leu Ala Pro Asp Asn Leu
                245                 250                 255

Phe Ala Ile Val Lys Leu Ser Ile Cys His Phe Gly Leu Glu Phe
                260                 265                 270
```

Gly Tyr Arg Val Ser Phe
               275

<210> SEQ ID NO 45
<211> LENGTH: 813
<212> TYPE: DNA
<213> ORGANISM: Ehrlichia canis
<220> FEATURE:
<223> OTHER INFORMATION: nucleic acid sequence of E. canis p28-9

<400> SEQUENCE: 45

| | | |
|---|---|---|
| atgaattaca aaagatttgt tgtaggtgtt acgctgagta catttgtttt tttcttatct | 60 |
| gatggtgctt tttctgatgc aaattttct gaagggagga gaggactta tataggtagt | 120 |
| cagtataaag ttggtattcc caattttagt aattttcag ctgaagaaac aattcctggt | 180 |
| attacaaaaa agattttgc gttaggtctt gataagtctg agataaatac tcacagcaat | 240 |
| tttacacgat catatgaccc tacttatgca agcagttttg cagggtttag tggtatcatt | 300 |
| ggatattatg ttaatgactt tagggtagaa tttgaaggtt cttatgagaa ttttgaacct | 360 |
| gaaagacaat ggtaccctga aatagccaa agctacaaat tttttgcttt gtctcgaaat | 420 |
| gctacaaata gtgataataa gtttatagta ctagagaata acggcgttgt tgacaagtct | 480 |
| cttaatgtaa atgtttgtta tgatattgct agtggtagta ttcctttagc accttatatg | 540 |
| tgtgctggtg ttggtgcaga ttatataaag tttttaggta tatcattgcc taagttttct | 600 |
| tatcaagtta agtttggtgt caactaccct ctaaatgtta atactatgtt gtttggtggg | 660 |
| ggttattacc ataaggttgt aggtgatagg catgagagag tagaaatagc ttaccatcct | 720 |
| actgcattat ctgacgttcc tagaactact tcagcttctg ctactttaaa tactgattat | 780 |
| tttggttggg agattggatt tagatttgcg cta | 813 |

<210> SEQ ID NO 46
<211> LENGTH: 271
<212> TYPE: PRT
<213> ORGANISM: Ehrlichia canis
<220> FEATURE:
<223> OTHER INFORMATION: amino acid sequence of E. canis p28-9 protein

<400> SEQUENCE: 46

Met Asn Tyr Lys Arg Phe Val Val Gly Val Thr Leu Ser Thr Phe
                 5                  10                  15

Val Phe Phe Leu Ser Asp Gly Ala Phe Ser Asp Ala Asn Phe Ser
                20                  25                  30

Glu Gly Arg Arg Gly Leu Tyr Ile Gly Ser Gln Tyr Lys Val Gly
                35                  40                  45

Ile Pro Asn Phe Ser Asn Phe Ser Ala Glu Glu Thr Ile Pro Gly
                50                  55                  60

Ile Thr Lys Lys Ile Phe Ala Leu Gly Leu Asp Lys Ser Glu Ile
                65                  70                  75

Asn Thr His Ser Asn Phe Thr Arg Ser Tyr Asp Pro Thr Tyr Ala
                80                  85                  90

Ser Ser Phe Ala Gly Phe Ser Gly Ile Ile Gly Tyr Tyr Val Asn
                95                  100                 105

Asp Phe Arg Val Glu Phe Glu Gly Ser Tyr Glu Asn Phe Glu Pro
                110                 115                 120

Glu Arg Gln Trp Tyr Pro Glu Asn Ser Gln Ser Tyr Lys Phe Phe
                125                 130                 135

-continued

| | | | | | | | | | | | | | | |
|---|---|---|---|---|---|---|---|---|---|---|---|---|---|---|
| Ala | Leu | Ser | Arg | Asn | Ala | Thr | Asn | Ser | Asp | Asn | Lys | Phe | Ile | Val |
| | | | | 140 | | | | | 145 | | | | | 150 |
| Leu | Glu | Asn | Asn | Gly | Val | Val | Asp | Lys | Ser | Leu | Asn | Val | Asn | Val |
| | | | | 155 | | | | | 160 | | | | | 165 |
| Cys | Tyr | Asp | Ile | Ala | Ser | Gly | Ser | Ile | Pro | Leu | Ala | Pro | Tyr | Met |
| | | | | 170 | | | | | 175 | | | | | 180 |
| Cys | Ala | Gly | Val | Gly | Ala | Asp | Tyr | Ile | Lys | Phe | Leu | Gly | Ile | Ser |
| | | | | 185 | | | | | 190 | | | | | 195 |
| Leu | Pro | Lys | Phe | Ser | Tyr | Gln | Val | Lys | Phe | Gly | Val | Asn | Tyr | Pro |
| | | | | 200 | | | | | 205 | | | | | 210 |
| Leu | Asn | Val | Asn | Thr | Met | Leu | Phe | Gly | Gly | Gly | Tyr | Tyr | His | Lys |
| | | | | 215 | | | | | 220 | | | | | 225 |
| Val | Val | Gly | Asp | Arg | His | Glu | Arg | Val | Glu | Ile | Ala | Tyr | His | Pro |
| | | | | 230 | | | | | 235 | | | | | 240 |
| Thr | Ala | Leu | Ser | Asp | Val | Pro | Arg | Thr | Thr | Ser | Ala | Ser | Ala | Thr |
| | | | | 245 | | | | | 250 | | | | | 255 |
| Leu | Asn | Thr | Asp | Tyr | Phe | Gly | Trp | Glu | Ile | Gly | Phe | Arg | Phe | Ala |
| | | | | 260 | | | | | 265 | | | | | 270 |
| Leu | | | | | | | | | | | | | | |
| 271 | | | | | | | | | | | | | | |

HOMOLOGOUS 28-KILODALTON IMMUNODOMINANT PROTEIN GENES OF *EHRLICHIA CANIS* AND USES THEREOF

CROSS-REFERENCE TO RELATED APPLICATION

This patent application is a divisional application of application Ser. No. 09/660,587, filed Sep. 12, 2000, now U.S. Pat. No. 6,392,023, which is a continuation-in-part of application Ser. No. 09/261,358, filed Mar. 3, 1999, now U.S. Pat. No. 6,403,780, which is a continuation-in-part of application Ser. No. 09/201,458, filed Nov. 30, 1998, now U.S. Pat. No. 6,458,942.

BACKGROUND OF THE INVENTION

1. Field of the Invention

The present invention relates generally to the field of molecular biology. More specifically, the present invention relates to molecular cloning and characterization of homologous 28-kDa protein genes in *Ehrlichia canis*, a multigene locus encoding the 28-kDa homologous proteins of *Ehrlichia canis* and uses thereof.

2. Description of the Related Art

Canine ehrlichiosis, also known as canine tropical pancytopenia, is a tick-borne rickettsial disease of dogs first described in Africa in 1935 and the United States in 1963 (Donatien and Lestoquard, 1935; Ewing, 1963). The disease became better recognized after an epizootic outbreak occurred in United States military dogs during the Vietnam War (Walker et al., 1970)

The etiologic agent of canine ehrlichiosis is *Ehrlichia canis*, a small, gram-negative, obligate intracellular bacterium which exhibits tropism for mononuclear phagocytes (Nyindo et al., 1971) and is transmitted by the brown dog tick, *Rhipicephalus sanguineus* (Groves et al., 1975). The progression of canine ehrlichiosis occurs in three phases, acute, subclinical and chronic. The acute phase is characterized by fever, anorexia, depression, lymphadenopathy and mild thrombocytopenia (Troy and Forrester, 1990). Dogs typically recover from the acute phase, but become persistently infected carriers of the organism without clinical signs of disease for months or even years (Harrus et al., 1998). A chronic phase develops in some cases that is characterized by thrombocytopenia, hyperglobulinemia, anorexia, emaciation, and hemorrhage, particularly epistaxis, followed by death (Troy and Forrester, 1990).

Regulation of surface antigenicity may be an important mechanism for the establishment of such persistent infections in the host. Although disease pathogenesis is poorly understood, multigene families described in members of the related genera *Ehrlichia*, *Anaplasma*, and *Cowdria* may be involved in variation of major surface antigen expression thereby evading immune surveillance. *Anaplasma marginale*, an organism closely related to *E. canis*, exhibits variation of major surface protein 3 (msp-3) genes resulting in antigenic polymorphism among strains (Alleman et al., 1997).

Molecular taxonomic analysis based on the 16S rRNA gene has determined that *E. canis* and *E. chaffeensis*, the etiologic agent of human monocytic ehrlichiosis (HME), are closely related (Anderson et al., 1991; Anderson et al., 1992; Dawson et al., 1991; Chen et al., 1994). Considerable cross reactivity of the 64, 47, 40, 30, 29 and 23-kDa antigens between *E. canis* and *E. chaffeensis* has been reported (Chen et al., 1994; Chen et al., 1997; Rikihisa et al., 1994; Rikihisa et al., 1992). Analysis of immunoreactive antigens with human and canine convalescent phase sera by immunoblot has resulted in the identification of numerous immunodominant proteins of *E. canis*, including a 30-kDa protein (Chen et al., 1997). In addition, a 30-kDa protein of *E. canis* has been described as a major immunodominant antigen recognized early in the immune response that is antigenically distinct from the 30-kDa protein of *E. chaffeensis* (Rikihisa et al., 1992; Rikihisa et al., 1994). Other immunodominant proteins of *E. canis* with molecular masses ranging from 20 to 30-kDa have also been identified (Brouqui et al., 1992; Nyindo et al., 1991; Chen et al., 1994; Chen et al., 1997).

Homologous 28-32 kDa immunodominant proteins encoded by multigene families have been reported in related organisms including, *E. chaffeensis* and *Cowdria ruminantium* (Sulsona et al., 1999; Ohashi et al., 1998a; Reddy et al., 1998). Recently, characterization of a 21 member multigene family encoding proteins of 23 to 28-kDa has been described in *E. chaffeensis* (Yu et al., 2000). The *E. chaffeensis* 28-kDa outer membrane proteins are surface exposed, and contain three major hypervariable regions (Ohashi et al., 1998a). The recombinant *E. chaffeensis* P28 appeared to provide protection against homologous challenge infection in mice, and antisera produced against the recombinant protein cross reacted with a 30-kDa protein of *E. canis* (Ohashi et al., 1998a). Diversity in the p28 gene among *E. chaffeensis* isolates has been reported (Yu et al., 1999a), and studies using monoclonal antibodies have further demonstrated diversity in the expressed P28 proteins (Yu et al., 1993). Conversely, complete conservation of a p28 genes in geographically different isolates of *E. canis* has been reported and suggests that *E. canis* may be conserved in North America (McBride et al., 1999, 2000).

The prior art is deficient in the lack of cloning and characterization of new homologous 28-kDa immunoreactive protein genes of *Ehrlichia canis* and a single multigene locus containing the homologous 28-kDa protein genes. Further, The prior art is deficient in the lack of recombinant proteins of such immunoreactive genes of *Ehrlichia canis*. The present invention fulfills this long-standing need and desire in the art.

SUMMARY OF THE INVENTION

Certain embodiments of the present invention describe the molecular cloning, sequencing, characterization, and expression of homologous mature 28-kDa immunoreactive protein genes of *Ehrlichia canis* (designated p28-1, -2, -3, -5, -6, -7, -9), and the identification of a single locus (10,677-bp) containing nine 28-kDa protein genes of *Ehrlichia canis* (p28-1 to p28-9). Eight of the p28 genes were located on one DNA strand, and one p28 gene was found on the complementary strand. The nucleic acid homology among the nine p28 gene members was 37 to 75%, and the amino acid homology ranged from 28 to 72%.

In one embodiment of the present invention, there are provided DNA sequences encoding a 30-kDa immunoreactive protein of *Ehrlichia canis*. Preferably, the protein has an amino acid sequence selected from the group consisting of SEQ ID No. 2, 4, 6, 40, 42, 44, 46 and the gene has a nucleic acid sequence selected from the group consisting of SEQ ID No. 1, 3, 5, 39, 41, 43, 45 and is a member of a polymorphic multiple gene family. Generally, the protein has an N-terminal signal sequence which may be cleaved after post-translational process resulting in the production of a mature 28-kDa protein. Furthermore, the genes encoding 28-kDa proteins are preferably contained in a single multigene locus, which has the size of 10,677 bp and encodes nine homologous 28-kDa proteins of *Ehrlichia canis*.

In another embodiment of the present invention, there is provided an expression vector comprising a gene encoding a 28-kDa immunoreactive protein of *Ehrlichia canis* and capable of expressing the gene when the vector is introduced into a cell.

In still another embodiment of the present invention, there is provided a recombinant protein comprising an amino acid sequence selected from the group consisting of SEQ ID No. 2, 4, 6, 40, 42, 44, and 46. Preferably, the amino acid sequence is encoded by a nucleic acid sequence selected from the group consisting of SEQ ID No. 1, 3, 5, 39, 41, 43, and 45. Preferably, the recombinant protein comprises four variable regions which may be surface exposed, hydrophilic and antigenic. The recombinant protein may be useful as an antigen.

In yet another embodiment of the present invention, there is provided a method of producing the recombinant protein, comprising the steps of obtaining a vector that comprises an expression region comprising a sequence encoding the amino acid sequence selected from the group consisting of SEQ ID No. 2, 4, 6, 40, 42, 44, and 46 operatively linked to a promoter; transfecting the vector into a cell; and culturing the cell under conditions effective for expression of the expression region.

The invention may also be described in certain embodiments as a method of inhibiting *Ehrlichia canis* infection in a subject comprising the steps of: identifying a subject prior to exposure or suspected of being exposed to or infected with *Ehrlichia canis*; and administering a composition comprising a 28-kDa antigen of *Ehrlichia canis* in an amount effective to inhibit an *Ehrlichia canis* infection. The inhibition may occur through any means such as, e.g., the stimulation of the subject's humoral or cellular immune responses, or by other means such as inhibiting the normal function of the 28-kDa antigen, or even competing with the antigen for interaction with some agent in the subject's body.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows nucleic acid sequence (SEQ ID No. 1) and deduced amino acid sequence (SEQ ID No. 2) of p28-7 gene including adjacent 5' and 3' non-coding sequences. The ATG start codon and TAA termination are shown in bold, and the 23 amino acid leader signal sequence is underlined.

FIG. 3 shows amino acid sequences alignment of p28-7 protein (ECa28-1, SEQ ID NO. 2), p28-5 protein (ECa28SA2, partial sequence, SEQ ID NO. 7), p28-4 protein (ECa28SA1, SEQ ID NO. 8), *E. chaffeensis* P28 (SEQ ID NO. 9), *E. chaffeensis* OMP-1 family (SEQ ID NOs: 10-14) and *C. ruminantium* MAP-1 protein (SEQ ID NO. 15). The p28-7 amino acid sequence is presented as the consensus sequence. Amino acids not shown are identical to p28-7 and are represented by a dot. Divergent amino acids are shown with the corresponding one letter abbreviation. Gaps introduced for maximal alignment of the amino acid sequences are denoted with a dash. Variable regions are underlined and denoted (VR1, VR2, VR3, and VR4). The arrows indicate the predicted signal peptidase cleavage site for the signal peptide.

FIG. 7 shows nucleic acid sequences and deduced amino acid sequences of the *E. canis* 28-kDa protein genes p28-5 (nucleotide 1-849: SEQ ID No. 3; amino acid sequence: SEQ ID No. 4) and p28-6 (nucleotide 1195-2031: SEQ ID No. 5; amino acid sequence: SEQ ID No. 6) including intergenic noncoding sequences (NC2, nucleotide 850-1194: SEQ ID No. 31). The ATG start codon and termination condons are shown in bold.

The scale measures the distance between sequences.

Figure 10:
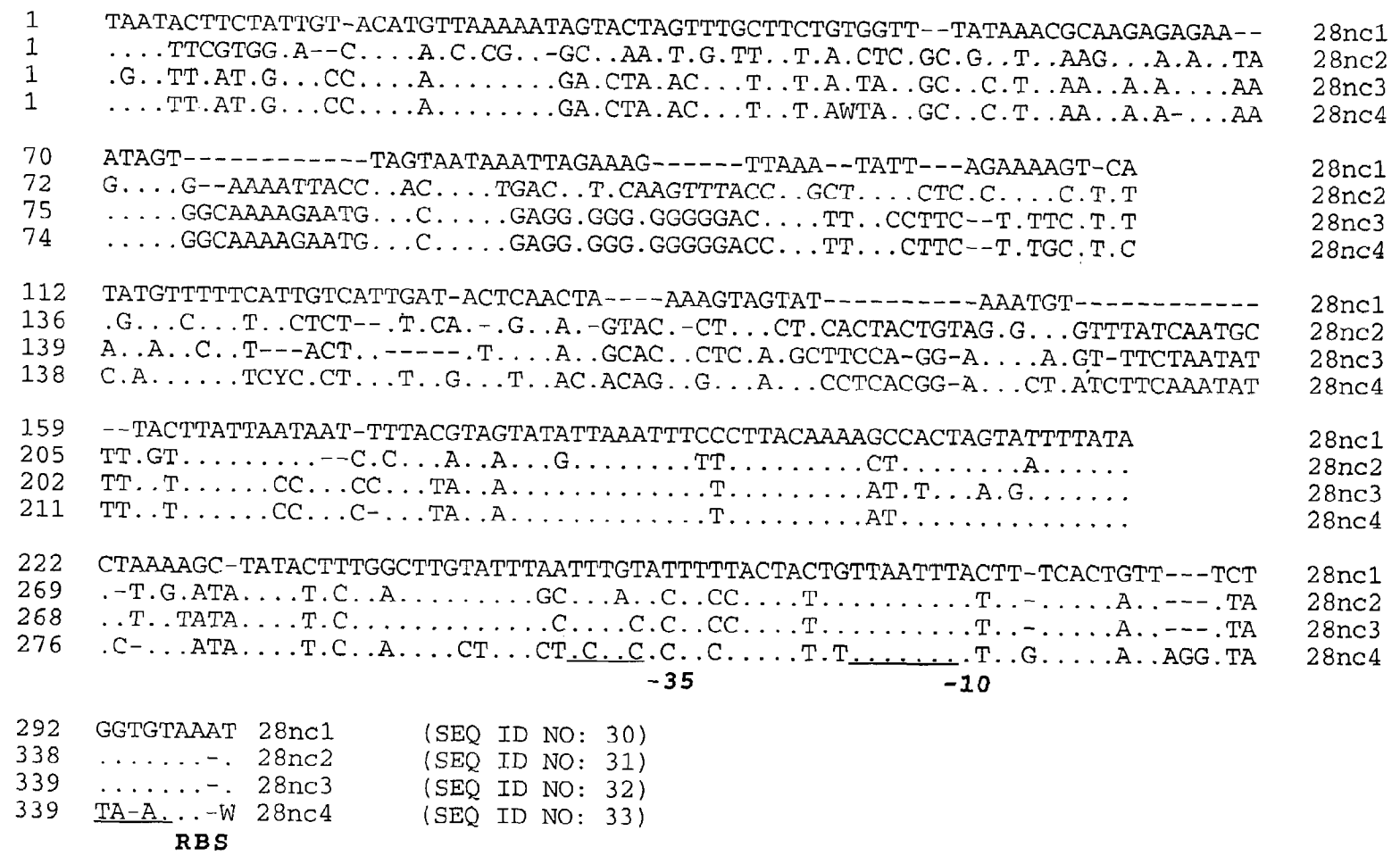

FIG. 10 shows alignment of E. canis 28-kDa protein gene intergenic noncoding nucleic acid sequences (SEQ ID Nos. 30-33). Nucleic acids not shown, denoted with a dot (.), are identical to noncoding region 1 (28NC1). Divergence is shown with the corresponding one letter abbreviation. Gaps introduced for maximal alignment of the amino acid sequences are denoted with a dash (–). Putative transcriptional promoter regions (–10 and –35) and ribosomal binding site (RBS) are boxed.

Figure 11:
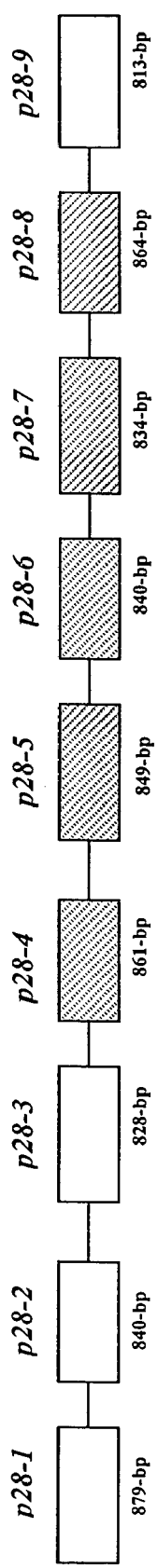

FIG. 11 shows schematic representation of the nine gene E. canis p28 locus (10,677-bp) indicating genomic orientation and intergenic noncoding regions. The p28 genes (p28-1, 2, 3, 9) (unshaded) were identified in Example 8. Shaded p28 genes have been identified previously and designated as follows: p28-4, p30a (Ohashi et al., 1998b) and ORF1 (Reddy et al., 1998); p28-5 and p28-6, (McBride, et. al., 2000); p28-7, p28 (McBride et al., 1999) and p30 (Ohashi et al., 1998b); and p28-8, p30-1 (Ohashi et al., 1998b).

Figure 12:
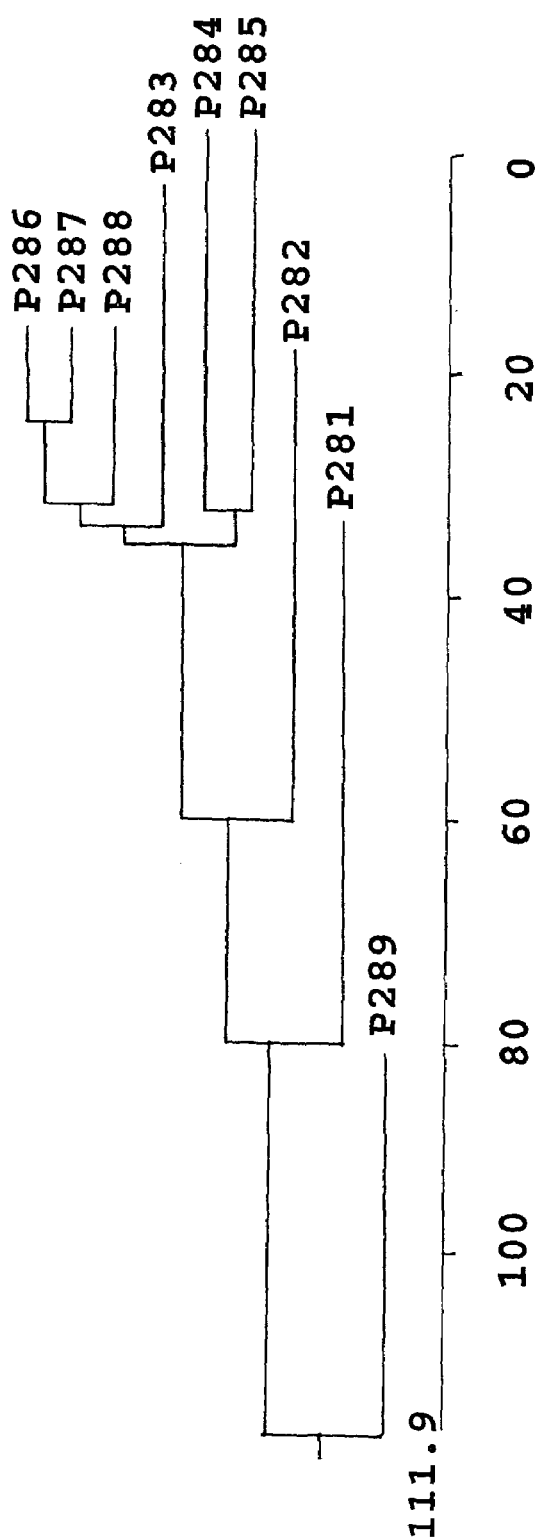

FIG. 12 shows phylogenetic relationships of E. canis P28-1 to P28-9 based on the amino acid sequences. The length of each pair of branches represents the distance between amino acid pairs. The scale measures the percentage of divergence between the sequences.

FIG. 13 shows nucleic acid sequence (SEQ ID No. 39) and deduced amino acid sequence (SEQ ID No. 40) of E. canis p28-1 gene.

FIG. 14 shows nucleic acid sequence (SEQ ID No. 41) and deduced amino acid sequence (SEQ ID No. 42) of E. canis p28-2 gene.

FIG. 15 shows nucleic acid sequence (SEQ ID No. 43) and deduced amino acid sequence (SEQ ID No. 44) of E. canis p28-3 gene.

FIG. 16 shows nucleic acid sequence (SEQ ID No. 45) and deduced amino acid sequence (SEQ ID No. 46) of E. canis p28-9 gene.

DETAILED DESCRIPTION OF THE INVENTION

The present invention describes cloning, sequencing and express ion of homologous genes encoding a 30-kilodalton (kDa) protein of Ehrlichia canis. A comparative molecular analysis of homologous genes among seven E. canis isolates and the E. chaffeensis omp-1 multigene family was also performed. Several new 28-kDa protein genes are identified as follows:

p28-7 (ECa28-1) has an 834-bp open reading frame encoding a protein of 278 amino acids (SEQ ID No. 2) with a predicted molecular mass of 30.5-kDa. An N-terminal signal sequence was identified suggesting that the protein is post-translationally modified to a mature protein of 27.7-kDa.

P28-6 (ECa28SA3) has an 840-bp open reading frame encoding a 280 amino acid protein (SEQ ID No. 6).

Using PCR to amplify 28-kDa protein genes of E. canis, a previously unsequenced region of p28-5 (Eca28SA2) was completed. Sequence analysis of p28-5 revealed an 849-bp open reading frame encoding a 283 amino acid protein (SEQ ID No. 4).

PCR amplification using primers specific for 28-kDa protein gene intergenic noncoding regions led to the sequencing of regions linking two previously separate loci, thereby identifying a single locus (5.592-kb) containing five 28-kDa protein genes (p28-4, -5, -6, -7 and -8). The five 28-kDa proteins were predicted to have signal peptides resulting in mature proteins, and had amino acid homology ranging from 51 to 72%. Analysis of intergenic regions revealed hypothetical promoter regions for each gene, suggesting that these genes may be independently and differentially expressed. Intergenic noncoding regions (28NC1-4) ranged in size from 299 to 355-bp, and were 48 to 71% homologous.

Furthermore, previously unknown regions of DNA upstream and downstream of the above five gene locus of tandemly arranged p28 genes were sequenced, and p28-1, -2, -3, and -9 were identified. Consequently, a nine gene E. canis p28 locus spanning 10, 677 bp was identified in the present invention.

The present invention is directed to, inter alia, homologous 28-kDa protein genes in Ehrlichia canis, p28-1, -2, -3, -6, -7, and p28-9, and a complete sequence of previously partially sequenced p28-5. Also disclosed is a multigene locus encoding nine homologous 28-kDa outer membrane proteins of Ehrlichia canis. Eight of the p28 genes were located on one DNA strand, and one p28 gene was found on the complementary strand. The nucleic acid homology among the nine p28 gene members was 37 to 75%, and the amino acid homology ranged from 28 to 72%.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

The invention includes a substantially pure DNA encoding a 28-kDa immunoreactive protein of Ehrlichia canis. The protein encoded by the DNA of this invention may share at least 80% sequence identity (preferably 85%, more preferably 90%, and most preferably 95%) with the amino acids listed in SEQ ID No. 2, 4, 6, 40, 42, 44 or 46. More preferably, the DNA includes the coding sequence of the nucleotides of SEQ ID No. 1, 3, 5, 39, 41, 43, 45, or a degenerate variant of such a sequence.

It is well known in the art that the amino acid sequence of a protein is determined by the nucleotide sequence of the DNA that encodes the protein. Because of the degeneracy of the genetic code (i.e., for most amino acids, more than one nucleotide triplet (codon) codes for a single amino acid), different nucleotide sequences can code for a particular amino acid, or polypeptide. Thus, the polynucleotide sequences of the subject invention also encompass those degenerate sequences that encode the polypeptides of the subject invention, or a fragment or variant thereof.

This invention also includes a substantially pure DNA containing a sequence of at least 15 consecutive nucleotides (preferably 20, more preferably 30, even more preferably 50, and most preferably all) of the region from the nucleotides listed in SEQ ID No 1, 3, 5, 39, 41, 43, or 45.

By "substantially pure DNA" is meant DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding a n additional polypeptide sequence, e.g., a fusion protein. Also included in the present invention is a recombinant DNA which includes a portion of the nucleotides listed in SEQ ID No 1, 3, 5, 39, 41, 43, or 45 which encodes a 28-kDa immunoreactive protein of *Ehrlichia canis*.

The DNA should have at least about 70% sequence identity to the coding sequence of the nucleotides listed in SEQ ID No 1, 3, 5, 39, 41, 43, or 45, preferably at least 75% (e.g. at least 80%); and most preferably at least 90% identity. The identity between two sequences is a direct function of the number of matching or identical positions. When a subunit position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

The present invention also comprises a vector comprising a DNA sequence coding for a which encodes a gene encoding a 28-kDa immunoreactive protein of *Ehrlichia canis* and said vector is capable of replication in a host which comprises, in operable linkage: a) an origin of replication; b) a promoter; and c) a DNA sequence coding for said protein. Preferably, the vector of the present invention contains a portion of the DNA sequence shown in SEQ ID No 1, 3, 5, 39, 41, 43, or 45.

A "vector" may be defined as a replicable nucleic acid construct, e.g., a plasmid or viral nucleic acid. Vectors may be used to amplify and/or express nucleic acid encoding a 28-kDa immunoreactive protein of *Ehrlichia canis*. An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation. Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

In general, expression vectors containing promoter sequences which facilitate the efficient transcription of the inserted DNA fragment are used in connection with the host. As used herein, the term "host" is meant to include not only prokaryotes but also eukaryotes such as yeast, plant and animal cells. A recombinant DNA molecule or gene which encodes a 28-kDa immunoreactive protein of *Ehrlichia canis* of the present invention can be used to transform a host using any of the techniques commonly known to those of ordinary skill in the art. Especially preferred is the use of a vector containing coding sequences for a gene encoding a 28-kDa immunoreactive protein of *Ehrlichia canis* of the present invention for purposes of prokaryote transformation.

Prokaryotic hosts may include *E. coli, S. tymphimurium, Serratia marcescens* and *Bacillus subtilis*. Eukaryotic hosts include yeasts such as *Pichia pastoris*, mammalian cells and insect cells. The transformed hosts can be fermented and cultured according to means known in the art to achieve optimal cell growth.

As used herein, the term "engineered" or "recombinant" cell is intended to refer to a cell into which a recombinant gene, such as a gene encoding an *Ehrlichia canis* antigen has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter not naturally associated with the particular introduced gene. In addition, the recombinant gene may be integrated into the host genome, or it may be contained in a vector, or in a bacterial genome transfected into the host cell.

The present invention is also drawn to substantially pure 28-30 kDa immunoreactive proteins of *E. canis* comprise of amino acid sequences listed in, for example, SEQ ID No. 2, 4, 6, 40, 42, 44, or 46.

By a "substantially pure protein" is meant a protein which has been separated from at least some of those components which naturally accompany it. Typically, the protein is substantially pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight. A substantially pure 28-kDa immunoreactive protein of *Ehrlichia canis* may be obtained, for example, by extraction from a natural source; by expression of a recombinant nucleic acid encoding a 28-kDa immunoreactive protein of *Ehrlichia canis*; or by chemically synthesizing the protein. Purity can be measured by any appropriate method, e.g., column chromatography such as immunoaffinity chromatography using a n antibody specific for a 28-kDa immunoreactive protein of *Ehrlichia canis*, polyacrylamide gel electrophoresis, or HPLC analysis. A protein is substantially free of naturally associated components when it is separated from at least some of those contaminants which accompany it in its natural state. Thus, a protein which is chemically synthesized or produced in a cellular system different from the cell from which it naturally originates will be, by definition, substantially free from its naturally associated components. Accordingly, substantially pure proteins include eukaryotic proteins synthesized in *E. coli*, other prokaryotes, or any other organism in which they do not naturally occur.

In addition to substantially full-length proteins, the invention also includes fragments (e.g., antigenic fragments) of the 28-kDa immunoreactive protein of *Ehrlichia canis* (SEQ ID No. 2, 4, 6, 40, 42, 44, or 46). As used herein, "fragment," as applied to a polypeptide, will ordinarily be at least 10 residues, more typically at least 20 residues, and preferably at least 30 (e.g., 50) residues in length, but less than the entire, intact sequence. Fragments of the 28-kDa immunoreactive protein of *Ehrlichia canis* can be generated by methods known to those skilled in the art, e.g., by enzymatic digestion of naturally occurring or recombinant 28-kDa immunoreactive protein of *Ehrlichia canis*, by recombinant DNA techniques using an expression vector that encodes a defined fragment of 28-kDa immunoreactive protein of *Ehrlichia canis*, or by chemical synthesis. The ability of a candidate fragment to exhibit a characteristic of 28-kDa immunoreactive protein of *Ehrlichia canis* (e.g., binding to an antibody specific for 28-kDa immunoreactive protein of *Ehrlichia canis*) can be assessed by methods described herein.

Purified 28-kDa immunoreactive protein of *Ehrlichia canis* or antigenic fragments of 28-kDa immunoreactive protein of *Ehrlichia canis* can be used to generate new antibodies or to test existing antibodies (e.g., as positive controls in a diagnostic assay) by employing standard protocols known to those skilled in the art.

As is well known in the art, a given polypeptide may vary in its immunogenicity. It is often necessary therefore to couple the immunogen (e.g., a polypeptide of the present invention) with a carrier. Exemplary and preferred carriers are keyhole limpet hemocyanin (KLH) and human serum albumin. Means for conjugating a polypeptide to a carrier protein are well known in the art and include glutaraldehyde, m-maleimidobenzoyl-N-hydroxysuccinimide ester, carbodiimide and bis-biazotized benzidine. It is also understood that the peptide may be conjugated to a protein by genetic engineering techniques that are well known in the art.

As is also well known in the art, immunogenicity to a particular immunogen can be enhanced by the use of nonspecific stimulators of the immune response known as adjuvants. Exemplary and preferred adjuvants include complete BCG, Detox, (RIBI, Immunochem Research Inc.) ISCOMS and aluminum hydroxide adjuvant (Superphos, Biosector).

Included in this invention are polyclonal antisera generated by using 28-kDa immunoreactive protein of *Ehrlichia canis* or a fragment of 28-kDa immunoreactive protein of *Ehrlichia canis* as the immunogen in, e.g., rabbits. Standard protocols for monoclonal and polyclonal antibody production known to those skilled in this art are employed. The monoclonal antibodies generated by this procedure can be screened for the ability to identify recombinant *Ehrlichia canis* cDNA clones, and to distinguish them from known cDNA clones.

The invention encompasses not only an intact monoclonal antibody, but also an immunologically-active antibody fragment, e.g., a Fab or (Fab)$_2$ fragment; an engineered single chain Fv molecule; or a chimeric molecule, e.g., an antibody which contains the binding specificity of one antibody, e.g., of murine origin, and the remaining portions of another antibody, e.g., of human origin.

In one embodiment, the antibody, or fragment thereof, may be linked to a toxin or to a detectable label, e.g. a radioactive label, non-radioactive isotopic label, fluorescent label, chemiluminescent label, paramagnetic label, enzyme label or calorimetric label. Those of ordinary skill in the art will know of these and other suitable labels which may be employed in accordance with the present invention. The binding of these labels to antibodies or fragments thereof can be accomplished using standard techniques commonly known to those of ordinary skill in the art.

It is also contemplated that pharmaceutical compositions may be prepared using the novel proteins of the present invention. In such a case, the pharmaceutical composition comprises the novel active composition(s) of the present invention and a pharmaceutically acceptable carrier. A person having ordinary skill in this art would readily be able to determine, without undue experimentation, the appropriate dosages and routes of administration of the active component of the present invention.

The phrase "pharmaceutically acceptable" refers to molecular entities and compositions that do not produce an allergic or similar untoward reaction when administered to a subject. The preparation of an aqueous composition that contains a protein as a n active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

A protein may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In one embodiment of the present invention, there are provided DNA sequences encoding a 30-kDa immunoreactive protein of *Ehrlichia canis*. Preferably, the protein has an amino acid sequence selected from the group consisting of SEQ ID No. 2, 4, 6, 40, 42, 44, 46, and the gene has a nucleic acid sequence selected from the group consisting of SEQ ID No. 1, 3, 5, 39, 41, 43, 45 and is a member of a polymorphic multiple gene family. More preferably, the protein has an N-terminal signal sequence which is cleaved after post-translational process resulting in the production of a mature 28-kDa protein. Still preferably, the DNAs encoding 28-kDa proteins are contained in a single multigene locus, which has the size of 10,677 bp and encodes nine homologous 28-kDa proteins of *Ehrlichia canis*.

In another embodiment of the present invention, there is provided an expression vector comprising a gene encoding a 28-kDa immunoreactive protein of *Ehrlichia canis* and capable of expressing the gene when the vector is introduced into a cell.

In still another embodiment of the present invention, there is provided a recombinant protein comprising an amino acid sequence selected from the group consisting of SEQ ID No. 2, 4, 6, 40, 42, 44, 46. Preferably, the amino acid sequence is encoded by a nucleic acid sequence selected from the group consisting of SEQ ID No. 1, 3, 5, 39, 41, 43, 45. More preferably, the recombinant protein comprises four variable regions which are surface exposed, hydrophilic and antigenic. Still preferably, the recombinant protein is an antigen.

In yet another embodiment of the present invention, there is provided a method of producing the recombinant protein, comprising the steps of obtaining a vector that comprises an expression region comprising a sequence encoding the amino acid sequence selected from the group consisting of SEQ ID No. 2, 4, 6, 40, 42, 44, 46 operatively linked to a promoter; transfecting the vector into a cell; and culturing the cell under conditions effective for expression of the expression region.

The invention may also be described in certain embodiments as a method of inhibiting *Ehrlichia canis* infection in a subject comprising the steps of: identifying a subject suspected of being exposed to or infected with *Ehrlichia canis*; and administering a composition comprising a 28-kDa antigen of *Ehrlichia canis* in an amount effective to inhibit an *Ehrlichia canis* infection. The inhibition may occur through any means such as, i.e. the stimulation of the subject's humoral or cellular immune responses, or by other means such as inhibiting the normal function of the 28-kDa antigen, or even competing with the antigen for interaction with some agent in the subject's body.

The following examples are given for the purpose of illustrating various embodiments of the invention and are not meant to limit the present invention in any fashion.

EXAMPLE 1

Sequencing Unknown 5' and 3' Regions of the ECa28-1 (p28-7) Gene

*Ehrlichiae* and Purification *Ehrlichia canis* (Florida strain and isolates Demon, D J, Jake, and Fuzzy) were provided by Dr. Edward Breitschwerdt, (College of Veterinary Medicine, North Carolina State University, Raleigh, N.C.). *E. canis* (Louisiana strain) was provided by Dr. Richard E. Corstvet (School of Veterinary Medicine, Louisiana State University, Baton Rouge, La.) and *E. canis* (Oklahoma strain) was provided by Dr. Jacqueline Dawson (Centers for Disease Control and Prevention, Atlanta, Ga.). Propagation of *ehrlichiae* was performed in DH82 cells with DMEM supplemented with 10% bovine calf serum and 2 mM L-glutamine at 37° C. The intracellular growth in DH82 cells was monitored by presence of *E. canis* morulae using general cytologic staining methods. Cells were harvested when 100% of the cells were infected with ehrlichiae and were then pelleted in a centrifuge at 17,000×g for 20 min. Cell pellets were disrupted with a Braun-Sonic 2000 sonicator twice at 40 W for 30 sec on ice. Ehrlichiae were purified as described previously (Weiss et al., 1975). The lysate was loaded onto discontinuous gradients of 42%-36%-30% renografin, and centrifuged at 80,000×g for 1 hr. Heavy and light bands containing ehrlichiae were collected and washed with sucrose-phosphate-glutamate buffer (SPG, 218 mM sucrose, 3.8 mM $KH_2PO_4$, 7.2 mM $K_2HPO_4$, 4.9 mM glutamate, pH 7.0) and pelleted by centrifugation.

Nucleic Acid Preparation *Ehrlichia canis* genomic DNA was prepared by resuspending the renografin-purified ehrlichiae in 600 μl of 10 mM Tris-HCl buffer (pH 7.5) with 1% sodium dodecyl sulfate (SDS, w/v) and 100 ng/ml of proteinase K as described previously (McBride et al., 1996). This mixture was incubated for 1 hr at 56° C., and the nucleic acids were extracted twice with a mixture of phenol/chloroform/isoamyl alcohol (24:24:1). DNA was pelleted by absolute ethanol precipitation, washed once with 70% ethanol, dried and resuspended in 10 mM Tris (pH 7.5). Plasmid DNA was purified by using High Pure Plasmid Isolation Kit (Boehringer Mannheim, Indianapolis, Ind.), and PCR products were purified using a QIAquick PCR Purification Kit (Qiagen, Santa Clarita, Calif.).

Cloning of ECa28-1 (p28-7) Gene The full length sequence of p28-7 gene was determined using a Universal GenomeWalker Kit (CLONTECH, Palo Alto, Calif.) according to the protocol supplied by the manufacturer. Genomic *E. canis* (Jake isolate) DNA was digested completely with five restriction enzymes (DraI, EcoRV, PvuII, ScaI, StuI) which produce blunt-ended DNA. An adapter (AP1) supplied in the kit was ligated to each end of *E. canis* DNA. The genomic libraries were used as templates to find the unknown DNA sequence of the p28-7 gene by PCR using a primer complementary to a known portion of the p28-7 sequence and a primer specific for the adapter AP1. Primers specific for p28-7 used for genome walking were designed from the known DNA sequence derived from PCR amplification of p28-7 with primers 793 (SEQ ID NO. 16) and 1330 (SEQ ID NO. 17). Primers 394 (5'-GCATTTCCACAGGATCATAGGTAA-3'; nucleotides 687-710, SEQ ID NO. 21) and 394C (5'-TTACCTATGATCCTGT GGAAATGC-3; nucleotides 710-687, SEQ ID NO. 22) were used in conjunction with supplied primer AP1 to amplify the unknown 5' and 3' regions of the p28-7 gene by PCR. A PCR product corresponding to the 5' region of the p28-7 gene amplified with primers 394C and AP1 (2000-bp) was sequenced unidirectionally with primer 793C (5'-GAGTA ACCAACAGCTCCTGC-3', SEQ ID No. 23). A PCR product corresponding to the 3' region of the p28-7 gene amplified with primers 394 and AP1 (580-bp) was sequenced bidirectionally with the same primers. Noncoding regions on the 5' and 3' regions adjacent to the open reading frame were sequenced, and primers EC28OM-F (5'-TCTACTTTGCACTTCC ACTATTGT-3', SEQ ID NO. 24) and EC28OM-R (5'-ATTCTTTTGCCACTATTT TTCTTT-3', SEQ ID NO. 25) complementary to these regions were designed in order to amplify the entire p28-7 gene.

DNA Sequencing DNA was sequenced with an ABI Prism 377 DNA Sequencer (Perkin-Elmer Applied Biosystems, Foster City, Calif.). The entire p28-7 genes of seven *E. canis* isolates (four from North Carolina, and one each from Oklahoma, Florida, and Louisiana) were amplified by PCR with primers EC28OM-F (SEQ ID No. 24) and EC28OM-R (SEQ ID No. 25) with a thermal cycling profile of 95° C. for 5 minutes, and 30 cycles of 95° C. for 30 seconds, 62° C. for 1 minutes, and 72° C. for 2 minutes and a 72° C. extension for 10 minutes. The resulting PCR products were bidirectionally sequenced with the same primers.

EXAMPLE 2

PCR Amplification, Cloning, Sequencing and Expression of *E. canis* ECa28-1 (p28-7) Gene Expression Vectors The entire *E. canis* p28-7 gene was PCR-amplified with primers-EC28OM-F and EC28OM-R and cloned into pCR2.1-TOPO TA cloning vector to obtain the desired set of restriction enzyme cleavage sites (Invitrogen, Carlsbad, Calif.). The insert was excised from pCR2.1-TOPO with BstX 1 and ligated into pcDNA 3.1 eukaryotic expression vector (Invitrogen, Carlsbad, Calif.) designated pcDNA3.1/EC28 for subsequent studies. The pcDNA3.1/EC28 plasmid was amplified, and the gene was excised with a KpnI-XbaI double digestion and directionally ligated into pThioHis prokaryotic expression vector (Invitrogen, Carlsbad, Calif.). The clone (designated pThioHis/EC28) produced a recombinant thioredoxin fusion protein in *Escherichia coli* BL21. The recombinant fusion protein was crudely purified in the insoluble phase by centrifugation. The control thioredoxin fusion protein was purified from soluble cell lysates under native conditions using nickel-NTA spin columns (Qiagen, Santa Clarita, Calif.).

Western Blot Analysis Recombinant *E. canis* p28-7 fusion protein was subjected to SDS-polyacrylamide gel electrophoresis (SDS-PAGE) on 4-15% Tris-HCl gradient gels (Bio-Rad, Hercules, Calif.) and transferred to pure nitrocellulose (Schleicher & Schuell, Keene, N.H.) using a semi-dry transfer cell (Bio-Rad, Hercules, Calif.). The membrane was incubated with convalescent phase antisera from an *E. canis*-infected dog diluted 1:5000 for 1 hour, washed, and then incubated with an anti-canine IgG (H & L) alkaline phosphatase-conjugated affinity-purified secondary antibody at 1:1000 for 1 hour (Kirkegaard & Perry Laboratories, Gaithersburg, Md.). Bound antibody was visualized with 5-bromo-4-chloro-3-indolyl phosphate/nitroblue tetrazolium (BCIP/NBT) substrate (Kirkegaard & Perry Laboratories, Gaithersburg, Md.).

Southern Blot Analysis To determine if multiple genes homologous to the p28-7 gene were present in the *E. canis* genome, a genomic Southern blot analysis was performed using a standard procedure (Sambrook et al. 1989). *E. canis* genomic DNA digested completely with each of the restriction enzymes BanII, EcoRV, HaeII, KpnI and SpeI, which do not cut within the p28-7 gene, and AseI which digests p28-7 at nucleotides 34, 43 and 656. The probe was produced by PCR amplification with primers EC28OM-F and EC28OM-R and digoxigenin (DIG)-labeled deoxynucleotide triphosphates (dNTPs) (Boehringer Mannheim, Indianapolis, Ind.) and digested with AseI. The digested probe (566-bp) was separated by agarose gel electrophoresis, gel-purified and then used for hybridization. The completely digested genomic *E. canis* DNA was electrophoresed and transferred to a nylon membrane (Boehringer Mannheim, Indianapolis, Ind.) and hybridized at 40° C. for 16 hr with the p28-7 gene DIG-labeled probe in DIG Easy Hyb buffer according to the manufacturer's protocol (Boehringer Mannheim, Indianapolis, Ind.). Bound probe was detected with a anti-DIG alkaline phosphatase-conjugated antibody and a luminescent substrate (Boehringer Mannheim, Indianapolis, Ind.) and exposed to BioMax scientific imaging film (Eastman Kodak, Rochester, N.Y.).

Sequence Analysis and Comparasion *E. chaffeensis* p28 and *C. ruminantium* map-1 DNA sequences were obtained from the National Center of Biotechnology Information (NCBI). Nucleotide and deduced amino acid sequences, and protein and phylogenetic analyses were performed with LASERGENE software (DNASTAR, Inc., Madison, Wis.). Analysis of post-translational processing was performed by the method of McGeoch and von Heijne for signal sequence recognition using the PSORT program (McGeoch, 1985; von Heijne, 1986)

Sequence analysis of p28-7 from seven different strains of *E. canis* was performed with primers designed to amplify the entire gene. Analysis revealed the sequence of this gene was conserved among the isolates from North Carolina (four), Louisiana, Florida and Oklahoma.

Results

Alignment of nucleic acid sequences from *E. chaffeensis* p28 and *Cowdria ruminantium* map-1 using the Jotun-Hein aligorithm produced a consensus sequence with regions of high homology (>90%). These homologous regions (nucleotides 313-332 and 823-843 of *C. ruminantium* map-1; 307-326 and 814-834 of *E. chaffeensis* p28) were targeted as primer annealing sites for PCR amplification. PCR amplification of the *E. canis* p28-7 gene was accomplished with primers 793 (5-GCAGGAGCTGTTGGTTACTC-3') (SEQ ID NO. 16) and 1330 (5'-CCTTCCTCCAAGTTCTATGCC-3') (SEQ ID NO. 17), resulting in a 518-bp PCR product. *E. canis* DNA was amplified with primers 793 and 1330 with a thermal cycling profile of 95° C. for 2 min, and 30 cycles of 95° C. for 30 sec, 62° C. for 1 min, 72° C. for 2 min followed by a 72° C. extension for 10 min and 4° C. hold. The nucleic acid sequence of the *E. canis* PCR product was obtained by sequencing the product directly with primers 793 and 1330.

Analysis of the sequence revealed an open reading frame encoding a protein of 170 amino acids, and alignment of the 518-bp sequence obtained from PCR amplification of *E. canis* with the DNA sequence of *E. chaffeensis* p28 gene revealed a similarity greater than 70%, indicating that the genes were homologous.

Adapter PCR with primers 394 and 793C was performed to determine the 5' and 3' segments of the sequence of the entire gene. Primer 394 produced four PCR products (3-kb, 2-kb, 1-kb, and 0.8-kb), and the 0.8-bp product was sequenced bidirectionally using primers 394 and API. The deduced sequence overlapped with the 3' end of the 518-bp product, extending the open reading frame 12-bp to a termination codon. An additional 625-bp of non-coding sequence at the 3' end of the p28-7 gene was also sequenced.

Primer 394C was used to amplify the 5' end of the p28-7 gene with supplied primer AP1. Amplification with these primers resulted in three PCR products (3.3, 3-kb, and 2-kb). The 2-kb fragment was sequenced unidirectionally with primer 793C. The sequence provided the putative start codon of the p28-7 gene and completed the 834-bp open reading frame encoding a protein of 278 amino acids. An additional 144-bp of readable sequence in the 5' noncoding region of the p28-7 gene was generated. Primers EC28OM-F and EC28OM-R were designed from complementary non-coding regions adjacent to the p28-7 gene.

Figure 2:
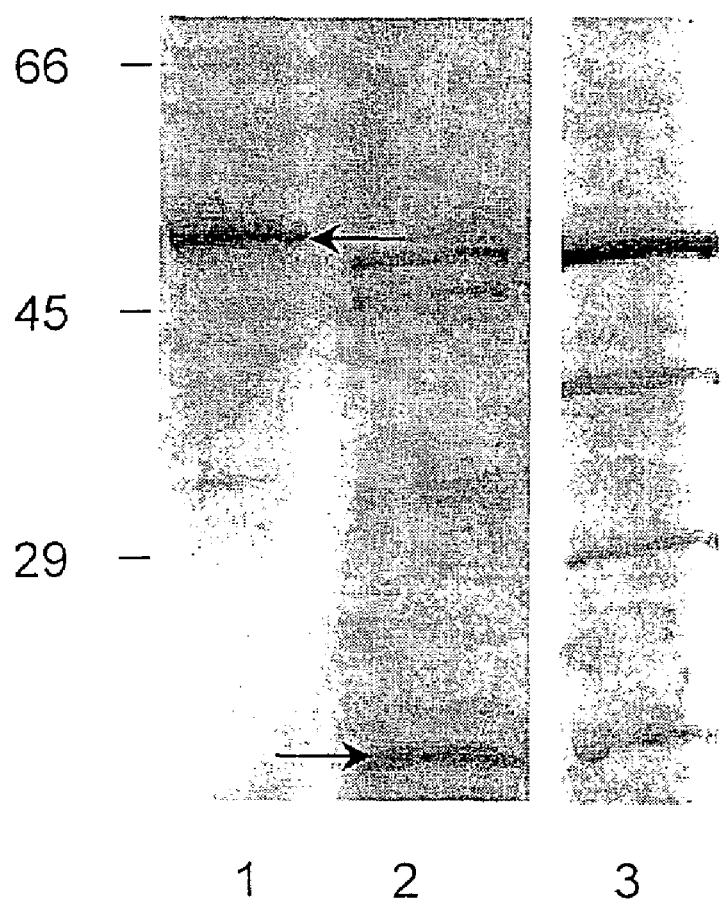
FIG. 2 shows SDS-PAGE of expressed 50-kDa recombinant p28-7-thioredoxin fusion protein (Lane 1, arrow) and 16-kDa thioredoxin control (Lane 2, arrow), and corresponding immunoblot of recombinant p28-7-thioredoxin fusion protein recognized by covalescent-phase *E. canis* canine antiserum (Lane 3). Thiroredoxin control was not detected by *E. canis* antiserum (not shown).

The PCR product amplified with these primers was sequenced directly with the same primers. The complete DNA sequence for the *E. canis* p28-7 gene (SEQ ID NO. 1) is shown in FIG. 1. The p28-7 PCR fragment amplified with these primers contained the entire open reading frame and 17 additional amino acids from the 5' non-coding primer region. The gene was directionally subcloned into pThioHis expression vector, and *E. coli* (BL21) were transformed with this construct. The expressed p28-7-thioredoxin fusion protein was insoluble. The expressed protein had an additional 114 amino acids associated with the thioredoxin, 5 amino acids for the enterokinase recognition site, and 32 amino acids from the multiple cloning site and 5' non-coding primer region at the N-terminus. Convalescent-phase antiserum from an *E. canis* infected dog recognized the expressed recombinant fusion protein, but did not react with the thioredoxin control (FIG. 2).

EXAMPLE 3

Sequence Homology of *E. canis* p28-7 Gene

The nucleic acid sequence of *E. canis* p28-7 (834-bp) and the *E. chaffeensis* omp-1 family of genes including signal sequences (p28-7, omp-1A, B, C, D, E, and F) were aligned using the Clustal method to examine homology between these genes (alignment not shown). Nucleic acid homology was equally conserved (68.9%) between *E. canis* p28-7, *E. chaffeensis* p28 and omp-1F. Other putative outer membrane protein genes in the *E. chaffeensis* omp-1 family, omp-1D (68.2%), omp-1E (66.7%), omp-1C (64.1%), *Cowdria ruminantium* map-1 (61.8%), *E. canis* 28-kDa protein 1 gene (60%) and 28-kDa protein 2 gene (partial) (59.5%) were also homologous to p28-7. *E. chaffeensis* omp-1B had the least nucleic acid homology (45.1%) with *E. canis* p28-7.

Figure 3A:
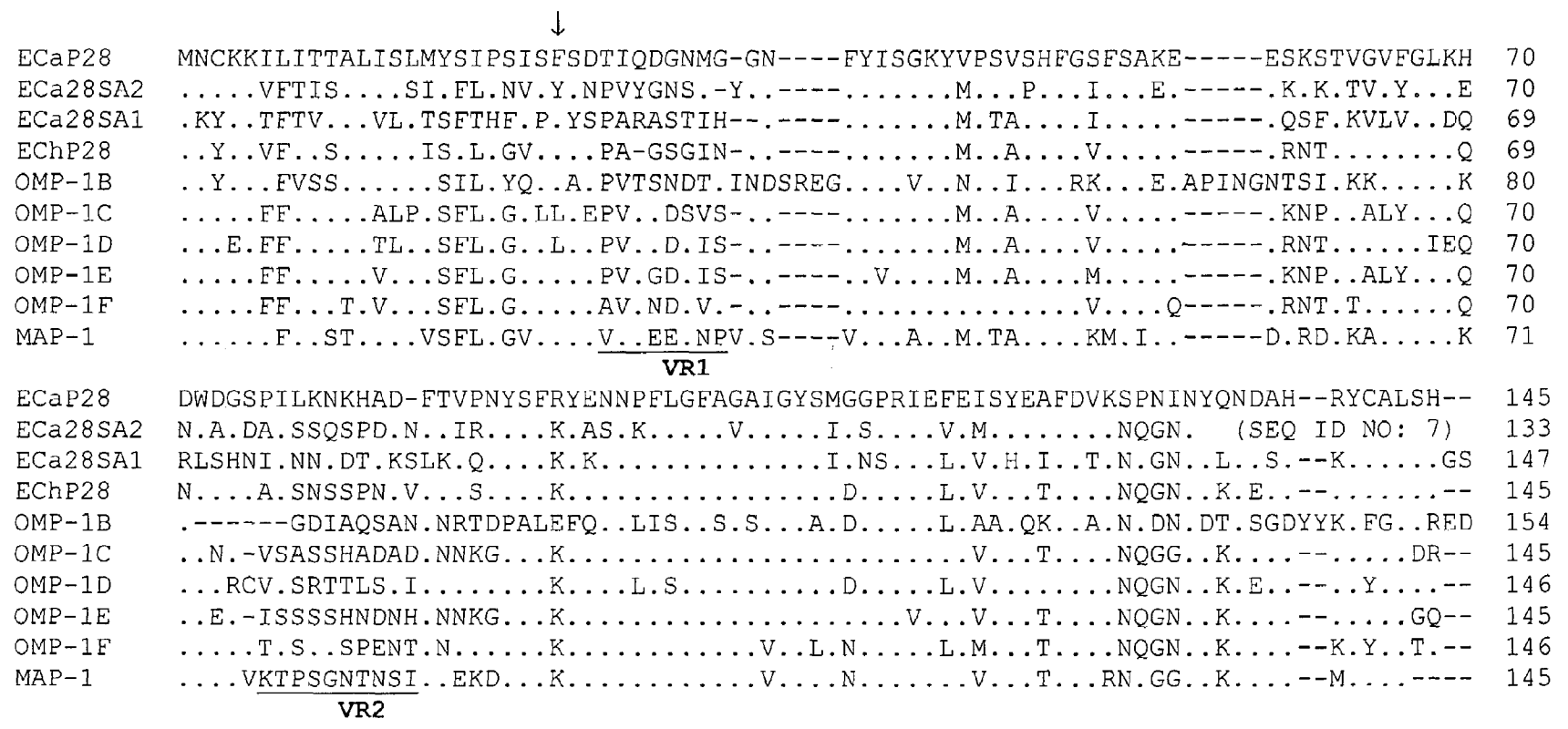
Figure 4:
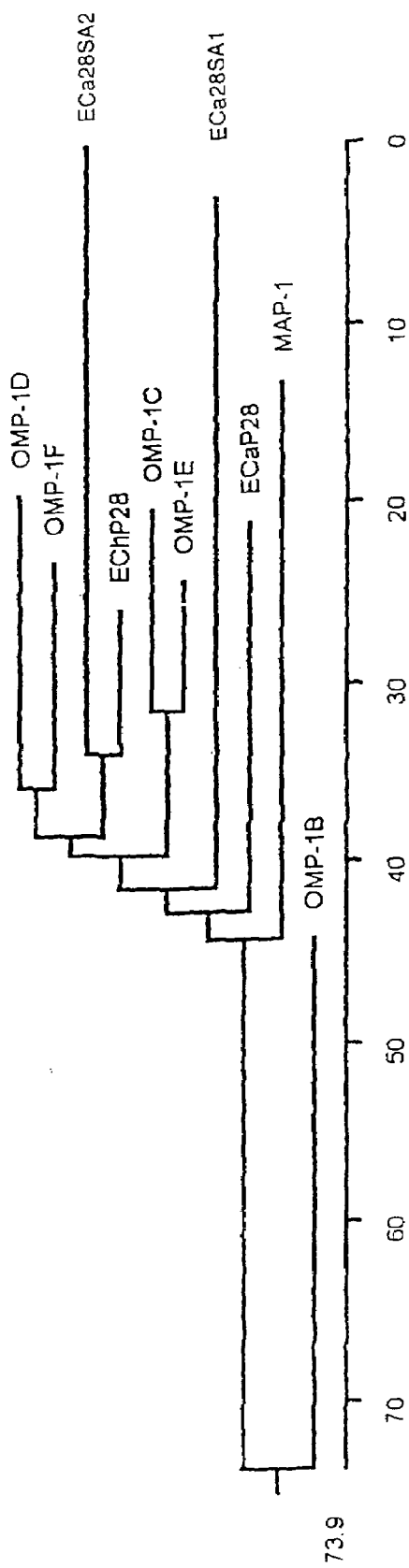
FIG. 4 shows phylogenetic relatedness of *E. canis* p28-7 (ECa28-1), p28-5 (ECa28SA2, partial sequence), p28-4 (ECa28SA1), members of the *E.chaffeensis* omp-1 multiple gene family, and *C. rumanintium* map-1 protein from deduced amino acid sequences utilizing unbalanced tree construction. The length of each pair of branches represents the distance between the amino acid sequence of the pairs. The scale measures the distance between sequences.

Alignment of the predicted amino acid sequences of *E. canis* P28-7 (SEQ ID NO. 2) and *E. chaffeensis* P28 revealed amino acid substitutions resulting in four variable regions (VR). Substitutions or deletions in the amino acid sequence and the locations of variable regions of *E. canis* P28-7 and the *E. chaffeensis* OMP-1 family were identified (FIG. 3). Amino acid comparison including the signal peptide revealed that *E. canis* P28-7 shared the most homology with OMP-1F (68%) of the *E. chaffeensis* OMP-1 family, followed by *E. chaffeensis* P28 (65.5%), OMP-1E (65.1%), OMP-1D (62.9%), OMP-1C (62.9%), *Cowdria ruminantium* MAP-1 (59.4%), *E. canis* 28-kDa protein 1 (55.6%) and 28-kDa protein 2 (partial) (53.6%), and OMP-1B (43.2%). The phylogenetic relationships based on amino acid sequences show that *E. canis* P28-7 and *C. ruminantium* MAP-1, *E. chaffeensis* OMP-1 proteins, and *E. canis* 28-kDa proteins 1 and 2 (partial) are related (FIG. 4).

EXAMPLE 4

Predicted Surface Probability and Immunoreactivity of *E. canis* P28-7

Figure 6:
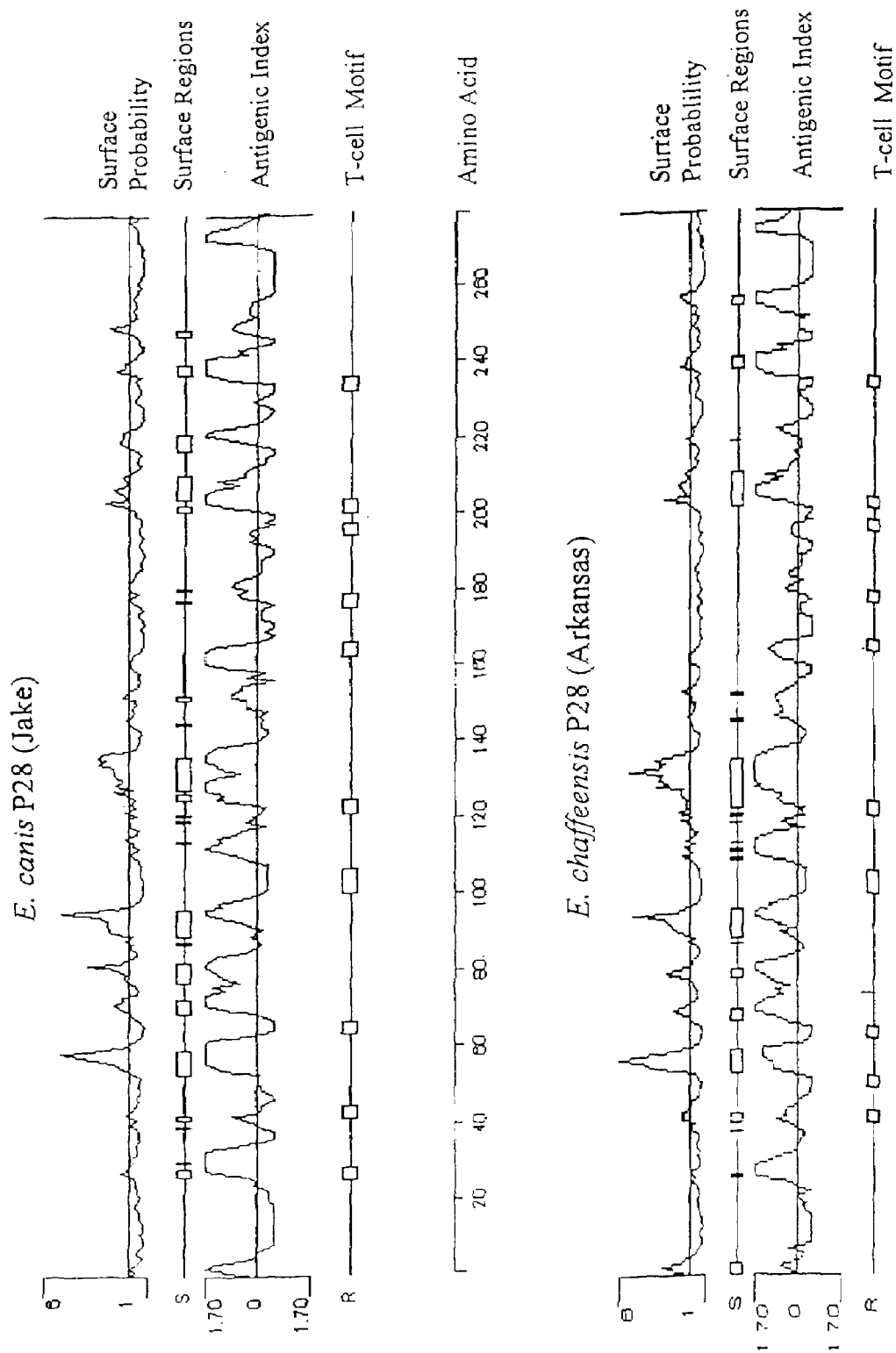
FIG. 6 shows comparison of predicted protein characteristics of *E. canis* p28-7 (ECa28-1, Jake strain) and *E. chaffeensis* P28 (Arkansas strain). Surface probability predicts the surface residues by using a window of hexapeptide. A surface residue is any residue with a >2.0 nm$^2$ of water accessible surface area. A hexapeptide with a value higher than 1 was considered as surface region. The antigenic index predicts potential antigenic determinants. The regions with a value above zero are potential antigenic determinants. T-cell motif locates the potential T-cell antigenic determinants by using a motif of 5 amino acids with residue 1-glycine or polar, residue 2-hydrophobic, residue 3-hydrophobic, residue 4-hydrophobic or proline, and residue 5-polar or glycine. The scale indicates amino acid positions.

Analysis of *E. canis* P28-7 using hydropathy and hydrophilicity profiles predicted surface-exposed regions on P28-7 (FIG. 6). Eight major surface-exposed regions consisting of 3 to 9 amino acids were identified on *E. canis* P28-7 and were similar to the profile of surface-exposed regions on *E. chaffeensis* P28 (FIG. 6). Five of the larger surface-exposed regions on *E. canis* P28-7 were located in the N-terminal region of the protein. Surface-exposed hydrophilic regions were found in all four of the variable regions of *E. canis* P28-7. Ten T-cell motifs were predicted in the P28-7 using the Rothbard-Taylor aligorithm (Rothbard and Taylor, 1988), and high antigenicity of the *E. canis* P28-7 was predicted by the Jameson-Wolf antigenicity aligorithm (FIG. 6) (Jameson and Wolf, 1988). Similarities in antigenicity and T-cell motifs were observed between *E. canis* P28-7 and *E. chaffeensis* P28.

EXAMPLE 5

Detection of Homologous Genomic Copies of *E. canis* p28-7 Gene

Figure 5:
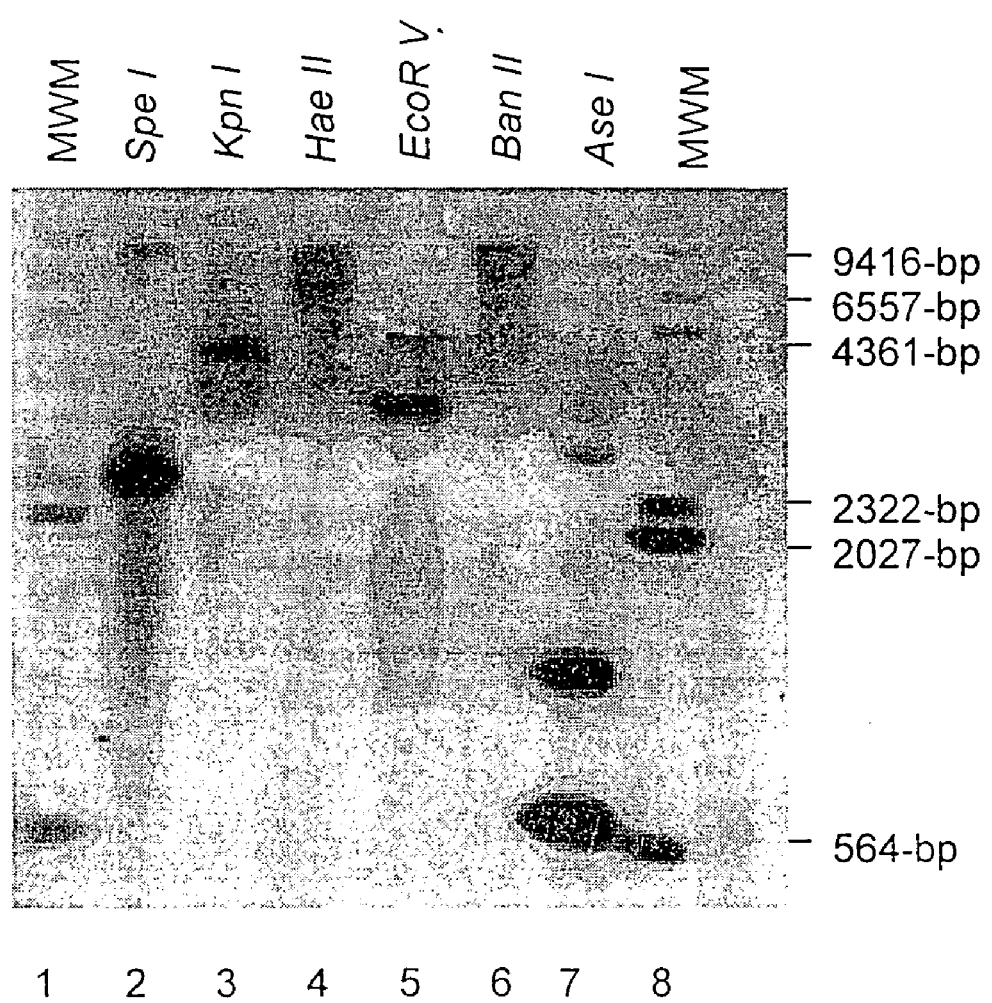
FIG. 5 shows Southern blot analysis of *E. canis* genomic DNA completely digested with six individual restriction enzymes and hybridized with a p28-7 DIG-labeled probe (Lanes 2-7); DIG-labeled molecular weight markers (Lanes 1 and 8).

Genomic Southern blot analysis of *E. canis* DNA completely digested independently with restriction enzymes BanII, EcoRV, HaeII, KpnI, SpeI, which do not have restriction endonuclease sites in the p28-7 gene, and AseI, which has internal restriction endonuclease sites at nucleotides 34, 43 and 656, revealed the presence of at least three homologous p28-7 gene copies (FIG. 5). Although *E. canis* p28-7 has internal Ase I internal restriction sites, the DIG-labeled probe used in the hybridization experiment targeted a region of the gene within a single DNA fragment generated by the AseI digestion of the gene. Digestion with AseI produced 3 bands (approximately 566-bp, 850-bp, and 3-kb) that hybridized with the p28-7 DNA probe indicating the presence of multiple genes homologous to p28-7 in the genome. Digestion with EcoRV and SpeI produced two bands that hybridized with the p28-7 gene probe.

EXAMPLE 6

PCR Amplification of *E. canis* ECa28SA2 (p28-5), ECa28SA3 (p28-6)

Genes and Identification of the Multiple Gene Locus

In order to specifically amplify possible unknown genes downstream of ECa28SA2 (p28-5), primer 46f specific for p28-5 (5'-ATATACTTCCTACCTAATGTCTCA-3', SEQ ID No. 18), and primer 1330 (SEQ ID No. 17) which targets a conserved region on the 3' end of p28-7 gene were used for amplification. The amplified product was gel purified and cloned into a TA cloning vector (Invitrogen, Santa Clarita, Calif.). The clone was sequenced bidirectionally with primers: M13 reverse from the vector, 46f, ECa28SA2 (5'-AGTGCAGAGTCTTCGGTTTC-3', SEQ ID No. 19), ECa5.3 (5'-GTTACTTGCGGAGGACAT-3', SEQ ID No. 20). DNA was amplified with a thermal cycling profile of 95° C. for 2 min, and 30 cycles of 95° C. for 30 sec, 48° C. for 1 min, 72° C. for 1 min followed by a 72° C. extension for 10 min and 4° C. hold.

A 2-kb PCR product was amplified with these primers that contained 2 open reading frames. The first open reading frame contained the known region of the p28-5 gene and a previously unsequenced 3' portion of the gene. Downstream from p28-5 an additional non identical, but homologous 28-kDa protein gene was found, and designated ECa28SA3 (p28-6).

Specific primers designated ECaSA3-2 (5'-CTAGGATTA GGTTATAGTATAAGTT-3', SEQ ID No. 26) corresponding to regions within p28-6 and primer 793C (SEQ ID No. 23) which anneals to a region with p28-7 were used to amplify the intergenic region between gene p28-6 and p28-7. DNA was amplified with a thermal cycling profile of 95° C. for 2 min, and 30 cycles of 95° C. for 30 sec, 50° C. for 1 min, 72° C. for 1 min followed by a 72° C. extension for 10 min and 4° C. hold.

Figure 8:
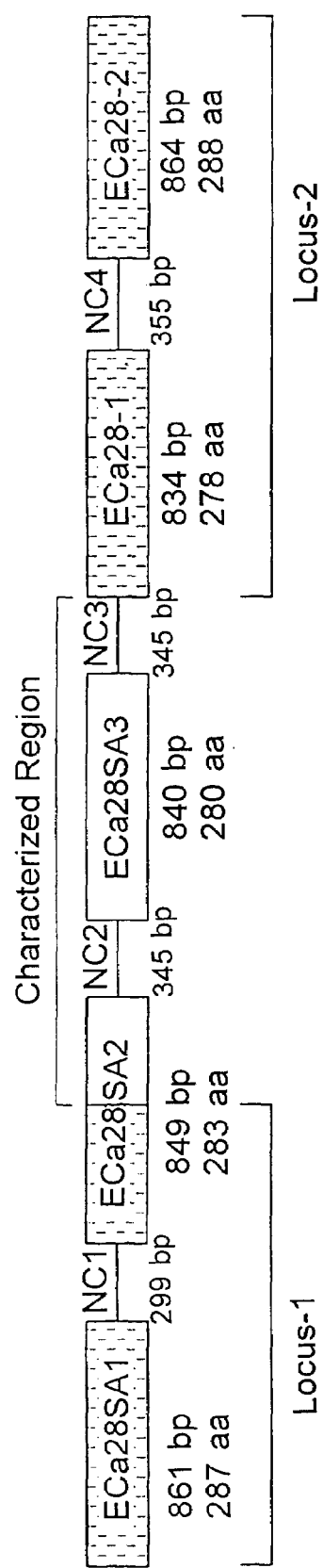
FIG. 8 shows schematic of the *E. canis* 28-kDa protein gene locus (5.592-Kb, containing five genes) indicating genomic orientation and intergenic noncoding regions (28NC1-4). The 28-kDa protein genes shown in Locus 1 and 2 (shaded) have been described (McBride et al., 1999; Reddy et al., 1998; Ohashi et al., 1998). The complete sequence of p28-5 and a new 28-kDa protein gene designated p28-6 was sequenced. The noncoding intergenic regions (28NC2-3) between p28-5, p28-6 and p28-7 were completed joining the previously unlinked loci 1 and 2.

An 800-bp PCR product was amplified which contained the 3' end of p28-6, the intergenic region between p28-6 and p28-7 (28NC3) and the 5' end of p28-7, joining the previously separate loci (FIG. 8). The 849-bp open reading frame of p28-5 encodes a 283 amino acid protein, and p28-6 has an 840-bp open reading frame encoding a 280 amino acid protein. The intergenic noncoding region between p28-6 and p28-7 was 345-bp in length (FIGS. 7 and 8)

EXAMPLE 7

Figure 9:
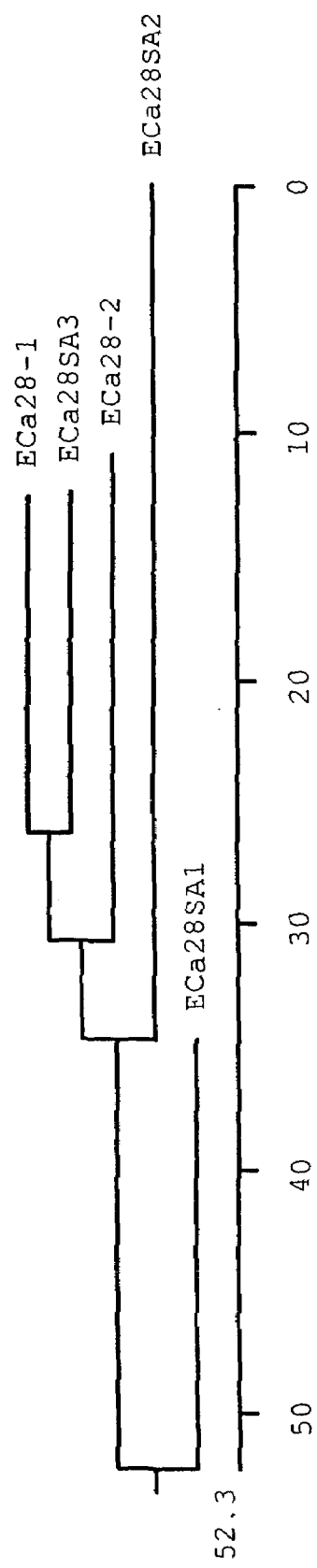
FIG. 9 shows phylogenetic relatedness of the *E. canis* 28-kDa protein gene p28-4 (ECa28SA1), p28-5 (ECa28SA2), p28-6 (ECa28SA3), p28-7 (ECa28-1) and p28-8 (ECa28-2) based on amino acid sequences utilizing unbalanced tree construction. The length of each pair of branches represents the distance between amino acid pairs.

Nucleic and Amino Acid Homology of *E. canis* p28-4, p29-5, p28-6, p28-7 and p28-9 proteins The nucleic and amino acid sequences of all five *E. canis* 28-kDa protein genes were aligned using the Clustal method to examine the homology between these genes. The nucleic acid homology ranged from 58 to 75% and a similar amino acid homology of ranging from 67 to 72% was observed between the *E. canis* 28-kDa protein gene members (FIG. 9).

Transcriptional Promoter Regions The intergenic regions between the 28-kDa protein genes were analyzed for promoter sequences by comparison with consensus *Escherichia coli* promoter regions and a promoter from *E. chaffeensis* (Yu et al., 1997; McClure, 1985). Putative promoter sequences including RBS, −10 and −35 regions were identified in 4 intergenic sequences corresponding to genes p28-5, p28-6, p28-7, and p28-8 (ECa28-2) (FIG. 10). The upstream noncoding region of p28-4 (ECa28SA1) is not known and was not analyzed.

N-Terminal Signal Sequence The amino acid sequence analysis revealed that entire *E. canis* p28-7 has a deduced molecular mass of 30.5-kDa and the entire p28-6 has a deduced molecular mass of 30.7-kDa. Both proteins have a predicted N-terminal signal peptide of 23 amino acids (MNCKKILITTALMSLMYYAPSIS, SEQ ID No. 27), which is similar to that predicted for *E. chaffeensis* P28 (MNYKKILITSALISLISSLPGV SFS, SEQ ID NO. 28), and the OMP-1 protein family (Yu et al., 1999a; Ohashi et al., 1998b).

A preferred cleavage site for signal peptidases (SIS; Ser-X-Ser) (Oliver, 1985) is found at amino acids 21, 22, and 23 of p28-7. An additional putative cleavage site at amino acid position 25 (MNCKKILITTALISLMYSIP-SISSFS, SEQ ID NO. 29) identical to the predicted cleavage site of *E. chaffeensis* P28 (SFS) was also present, and would result in a mature p28-7 with a predicted molecular mass of 27.7-kDa. Signal cleavage site of the previously reported partial sequence of p28-5 is predicted at amino acid 30. However, signal sequence analysis predicted that p28-4 had an uncleavable signal sequence.

Summary

Proteins of similar molecular mass have been identified and cloned from multiple rickettsial agents including *E. canis*, *E. chaffeensis*, and *C. ruminantium* (Reddy et al., 1998; Jongejan et al., 1993; Ohashi et al., 1998). A single locus in *Ehrlichia chaffeensis* with 6 homologous p28 genes, and 2 loci in *E. canis*, each containing some homologous 28-kDa protein genes have been previously described.

The present invention demonstrated the cloning, expression and characterization of genes encoding mature 28-kDa proteins of *E. canis* that are homologous to the omp-1 multiple gene family of *E. chaffeensis* and the *C. ruminantium* map-1 gene. Two new 28-kDa protein genes were identidfied, p28-7 and p28-6. Another *E.canis* 28-kDa protein gene, p28-5, partially sequenced previously (Reddy et al., 1998), was sequenced completely in the present invention. Also disclosed is the identification and characterization of a single locus in *E.canis* containing five *E.canis* 28-kDa protein genes (p28-4, p28-5, p28-6, p28-7 and p28-8).

The *E.canis* 28-kDa proteins are homologous to *E.chaffeensis* OMP-1 family and the MAP-1 protein of *C. ruminantium*. The most homologous *E. canis* 28-kDa proteins (p28-6, p28-7 and p28-8) are sequentially arranged in the locus. Homology of these proteins ranged from 67.5% to 72.3%. Divergence among these 28-kDa proteins was 27.3% to 38.6%. *E. canis* 28-kDa proteins p28-4 and p28-5 were the least homologous with homology ranging from 50.9% to 59.4% and divergence of 53.3 to 69.9%. Differences between the genes lies primarily in the four hypervariable regions and suggests that these regions are surface exposed and subject to selective pressure by the immune system. Conservation of p28-7 among seven *E. canis* isolates has been reported (McBride et al., 1999), suggesting that *E. canis* may be clonal in North America. Conversely, significant diversity of p28 among *E. chaffeensis* isolates has been reported (Yu et al., 1999a).

All of the *E. canis* 28-kDa proteins appear to be post translationally processed from a 30-kD protein to a mature 28-kD protein. Recently, a signal sequence was identified on *E. chaffeensis* P28 (Yu et al., 1999a), and N-terminal amino acid sequencing has verified that the protein is post-translationally processed resulting in cleavage of the signal sequence to produce a mature protein (Ohashi et al., 1998). The leader sequences of OMP-1F and OMP-1E have also been proposed as leader signal peptides (Ohashi et al., 1998). Signal sequences identified on *E. chaffeensis* OMP-1F, OMP-1E and P28 are homologous to the leader sequence of *E. canis* 28-kDa protein. Promoter sequences for the p28 genes have not been determined experimentally, but putative promoter regions were identified by comparison with consensus sequences of the RBS, −10 and −35 promoter regions of *E. coli* and other ehrlichiae (Yu et al., 1997; McClure, 1985). Such promoter sequences would allow each gene to potentially be transcribed and translated, suggesting that these genes may be differentially expressed in the host. Persistence of infection in dogs may be related to differential expression of p28 genes resulting in antigenic changes in vivo, thus allowing the organism to evade the immune response.

The *E. canis* 28-kda protein genes were found to exhibit nucleic acid and amino acid sequence homology with the *E. chaffeensis* omp-1 gene family and *C. ruminantium* map-1 gene. Previous studies have identified a 30-kDa protein of *E. canis* that reacts with convalescent phase antisera against *E. chaffeensis*, but was believed to be antigenically distinct (Rikihisa et al., 1994). Findings based on comparison of amino acid substitutions in four variable regions of *E. canis* 28-kDa proteins support this possibility. Together these findings also suggest that the amino acids responsible for the antigenic differences between *E. canis* and *E. chaffeensis* P28 are located in these variable regions and are readily accessible to the immune system.

It was reported that immunoreactive peptides were located in the variable regions of the 28-kDa proteins of *C. ruminantium*, *E. chaffeensis* and *E. canis* (Reddy et al., 1998). Analysis of *E. canis* and *E. chaffeensis* P28 revealed that all of the variable regions have predicted surface-exposed amino acids. A study in dogs demonstrated lack of cross protection between *E. canis* and *E. chaffeensis* (Dawson and Ewing, 1992). This observation may be related to antigenic differences in the variable regions of P28 as well as in other immunologically important antigens of these *ehrlichial* species. Another study found that convalescent phase human antisera from *E. chaffeensis*-infected patients recognized 29/28-kDa protein(s) of *E. chaffeensis* and also reacted with homologous proteins of *E. canis* (Chen et al., 1997). Homologous and crossreactive epitopes on the *E.*

*canis* 28-kDa protein and *E. chaffeensis* P28 appear to be recognized by the immune system.

*E. canis* 28-kDa proteins may be important immunoprotective antigens. Several reports have demonstrated that the 30-kDa antigen of *E. canis* exhibits strong immunoreactivity (Rikihisa et al., 1994; Rikihisa et al., 1992). Antibodies in convalescent phase antisera from humans and dogs have consistently reacted with proteins in this size range from *E. chaffeensis* and *E. canis*, suggesting that they may be important immunoprotective antigens (Rikihisa et al., 1994; Chen et al., 1994; Chen et al., 1997). In addition, antibodies to 30, 24 and 21-kDa proteins developed early in the immune response to *E. canis* (Rikihisa et al., 1994; Rikihisa et al., 1992), suggesting that these proteins may be especially important in the immune responses in the acute stage of disease. Recently, a family of homologous genes encoding outer membrane proteins with molecular masses of 28-kDa have been identified in *E. chaffeensis*, and mice immunized with recombinant *E. chaffeensis* P28 appeared to have developed immunity against homologous challenge (Ohashi et al., 1998). The P28 of *E. chaffeensis* has been demonstrated to be present in the outer membrane, and immuno-electron microscopy has localized the P28 on the surface on the organism, and thus suggesting that it may serve as an adhesin (Ohashi et al., 1998). It is likely that the 28-kDa proteins of *E. canis* identified in this study have the same location and possibly serve a similar function.

Comparison of p28-7 from different strains of *E. canis* revealed that the gene is apparently completely conserved. Studies involving *E. chaffeensis* have demonstrated immunologic and molecular evidence of diversity. Patients infected with *E. chaffeensis* have variable immunoreactivity to the 29/28-kDa proteins, suggesting that there is antigenic diversity (Chen et al., 1997). Recently molecular evidence has been generated to support antigenic diversity in the p28 gene from *E. chaffeensis* (Yu et al., 1999a). A comparison of five *E. chaffeensis* isolates revealed that two isolates (Sapulpa and St. Vincent) were 100% identical, but three others (Arkansas, Jax, 91HE17) were divergent by as much as 13.4% at the amino acid level. The conservation of *E. canis* p28-7 suggests that *E. canis* strains found in the United States may be genetically identical, and thus *E. canis* 28-kDa protein is an attractive vaccine candidate for canine ehrlichiosis in the United States. Further analysis of *E. canis* isolates outside the United States may provide information regarding the origin and evolution of *E. canis*. Conservation of the 28-kDa protein makes it an important potential candidate for reliable serodiagnosis of canine ehrlichiosis.

The role of multiple homologous genes is not known at this point; however, persistence of *E.canis* infections in dogs could conceivably be related to antigenic variation due to variable expression of homologous 28-kDa protein genes, thus enabling *E. canis* to evade immune surveillance. Variation of msp-3 genes in *A. marginale* is partially responsible for variation in the MSP-3 protein, resulting in persistent infections (Alleman et al., 1997). Studies to examine 28-kDa protein gene expression by *E. canis* in acutely and chronically infected dogs would provide insight into the role of the 28-kDa protein gene family in persistence of infection.

EXAMPLE 8

Identification of *E. canis* p28-1, p28-2, p28-3 and p28-9 Genes

Unknown regions of DNA upstream and downstream of the five gene locus of tandemly arranged p28 genes described above were sequenced by designing gene specific primers for p28-1 (ECa28-75C) and p28-5 (ECa28-5-818f) to extend the p28 gene locus bidirectionally. Multiple gene walks were performed to obtain the unknown sequence as follows: 1.9-kp downstream of the 5 gene locus was amplified and sequenced using primers p28-5-818f (5'-TTA AAC ATA TGC CAC TTC GGA CTA-3', SEQ ID No. 34), producing a 900-bp amplicon, and 1191 (5'-TAT GAT CGT GTA AAA TTG CTG TGA GTA T-3', SEQ ID No. 35), producing a 1-kb amplicon. The 3.67-kbp of DNA upstream of the five gene locus was amplified and sequenced with primers ECa28-75C (5'-TAC TGG CAC GTG CTG GAC TA-3', SEQ ID No. 36), producing a 1.6-kbp amplicon; ECa5'-1600 (5'-CAC CAA TAA ATG CAG AGA CTT C-3', SEQ ID No. 37), producing a 1.6-kbp amplicon; and 3125 (5'-AAT CCA TCA TTT CTC ATT ACA GTG TG-3', SEQ ID No. 38), producing a 800-bp amplicon. The locus of nine tandemly arranged genes consisting of the four new p28 genes, and the five p28 genes described above were designated p28-1 through p28-9 (FIG. 11).

The nucleic acid and amino acid sequences of the *E. canis* p28 genes were aligned using the Clustal method to examine the homology between these genes. Homology of these proteins ranged from 67.5% to 75%, and divergence among these P28 proteins was 26.9% to 38%. *E. canis* P28 proteins P28-1, P28-2, and P28-9 were the least homologous with the other p28 genes ranging from 37% to 49% and divergence of 53 to 77%. The nucleic acid homology of the nine p28 genes ranged from 28 to 72%. The phylogenetic relationships based on the *E. canis* p28 amino acid sequences are shown in FIG. 12.

Nucleotide sequence and accession numbers. The GenBank accession numbers for the nucleic acid and amino acid sequences for the complete nine gene *E. canis* (Jake strain) p28 gene locus is AF082744. This accession number was originally assigned to p28-7, but has been updated with the sequence of the nine gene p28 locus, which includes p28-7. GenBank accession numbers for nucleic acid and amino acid sequences of p28-7 in other *E. canis* isolates described in this study are: Louisiana, AF082745; Oklahoma, AF082746; Demon, AF082747; DJ, AF082748; Fuzzy, AF082749; Florida, AF082750.

Multiple bands in the 28-kilodalton range have been observed by immunoblots of convalescent sera from *E. canis* infected dogs (Rikihisa et al., 1994), and expression of multiple p28 proteins could be an explanation for this observation. Southern blot studies suggest that other p28 genes, in addition to the five members of this locus, are present in the genome (McBride et al., 1999; Ohashi et al., 1998b).

In this study a single gene locus containing nine tandemly arranged *E. canis* p28 genes encoding homologous, but nonidentical, p28 genes was identified. The nine gene locus included four new p28 genes (FIGS. 13-16) and five tandemly arranged p28 genes that were reported above. Eight of the p28 genes were located on one DNA strand, and one p28 gene was found on the complementary strand. The nucleic acid homology among the nine p28 gene members was 37 to 75%, and the amino acid homology ranged from 28 to 72%.

The P28s of *E. canis* were found to be as closely related to 28-kilodalton proteins of other species such as *E. chaffeensis* as they are to themselves (McBride et al., 2000). Differences among the proteins are found primarily in several major hypervariable regions and suggest that these regions are surface exposed and subject to selective pressure by the immune system (McBride et al., 2000).

Conservation of an *E. canis* p28 gene (p28-7) among seven geographically different isolates has been reported (McBride et al., 1999), suggesting that *E.canis* may be highly conserved in North America. Similarly, the 120-kDa glycoprotein of *E. canis* is also conserved among isolates in the United States (Yu et al., 1997). In contrast, both the 120-kDa and the 28-kDa protein genes of *E. chaffeensis* are divergent among isolates (Yu et al., 1999a; Chen et al., 1997). The diversity of the 28-kDa protein gene of *E. chaffeensis* appeared to result from point mutations in the hypervariable regions perhaps due to selective immune pressure (Yu et al., 1999a). These data suggest that *E. canis* may have been introduced into North America relatively recently, and this may account for the conservation that was observed among isolates. The conservation of p28 genes in *E. canis* isolates may provide an opportunity to develop vaccine and serodiagnostic antigens that are particularly effective for disease prevention and serodiagnosis. A mixture of the P28s may provide the most reliable serodiagnostic test, but serodiagnosis with a single P28 has been reported to be useful for immunodiagnosis (Ohashi et al., 1998b; McBride et al., 1999).

The following references were cited herein.

Alleman A. R., et al., (1997) *Infect Immun* 65: 156-163.
Anderson B. E., et al., (1991) *J Clin Microbiol* 29: 2838-2842.
Anderson B. E., et al., (1992) *Int J Syst Bacteriol* 42: 299-302.
Brouqui P., et al., (1992) *J Clin Microbiol* 30: 1062-1066.
Chen S. M., et al., (1997) *Clin Diag Lab Immunol* 4: 731-735.
Chen S. M., et al., (1994) *Am J Trop Med Hyg* 50: 52-58.
Dawson J. E., et al., (1992) *Am J Vet Res* 53: 1322-1327.
Dawson J. E., et al., (1991) *J Infect Dis* 163: 564-567.
Donatien, et al., (1935) *Bull Soc Pathol Exot* 28: 418-9.
Ewing, (1963) *J Am Vet Med Assoc* 143: 503-6.
Groves M. G., et al., (1975) *Am J Vet Res* 36: 937-940.
Harrus S., et al., (1998) *J Clin Microbiol* 36: 73-76.
Jameson B. A., et al., (1988) *CABIOS* 4: 181-186.
Jongejan F., et al., (1993) *Rev Elev Med Vet Pays Trop* 46: 145-152.
McBride J. W., et al., (1996) *J Vet Diag Invest* 8: 441-447.
McBride, et al.,. (1999) *Clin Diagn Lab Immunol.* 6: 392-399.
McBride, et al.,. (2000) *Gene*; In press
McClure, (1985) *Ann Rev Biochem* 54: 171-204.
McGeoch D. J. (1985) *Virus Res* 3: 271-286.
Nyindo M., et al., (1991) *Am J Vet Res* 52: 1225-1230.
Nyindo, et al., (1971) *Am J Vet Res* 32: 1651-58.
Ohashi, et al., (1998a) *Infect Immun* 66: 132-9.
Ohashi, et al., (1998b) *J Clin Microb* 36: 2671-80
Reddy, et al., (1998) *Biochem Biophys Res Comm* 247: 636-43.
Rikihisa, et al., (1994) *J Clin Microbiol* 32: 2107-12.
Rothbard J. B., et al., (1988) *The EMBO J7*: 93-100.
Sambrook J., et al., (1989) *In Molecular Cloning: A Laboratory Manual.* Cold Spring Harbor: Cold Spring Harbor Press.
Sulsona et al., (1999) *Biochem. Biophys. Res. Commun.* 257: 300-305.
Troy G. C., et al., (1990) Canine ehrlichiosis. In *Infectious diseases of the dog and cat.* Green C. E. (ed). Philidelphia: W. B. Sauders Co.
von Heijne, (1986) *Nucl Acids Res* 14: 4683-90.
Walker, et al., (1970) *J Am Vet Med Assoc* 157: 43-55.
Weiss E., et al., (1975) *Appl Microbiol* 30: 456-463.
Yu et al., (1993) *J. Clin. Microbiol.* 31: 3284-3288.
Yu, et al., (1997) *Gene* 184: 149-154.
Yu, et al., (1999a) *J. Clin. Microbiol.* 37: 1137-1143.
Yu et al., (2000) *Gene* 248: 59-68.

Any patents or publications mentioned in this specification are indicative of the levels of those skilled in the art to which the invention pertains. These patents and publications are herein incorporated by reference to the same extent as if each individual publication was individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of inducing an immune response against *Ehrlichia canis* in a subject comprising the steps of:

identifying a subject prior to exposure or suspected of being exposed to or infected with *Ehrlichia canis*; and administering a composition comprising a 28-kDa antigen of *Ehrlichia canis*, wherein said 28-kDa antigen is a recombinant protein comprising an amino acid sequence selected from the group consisting of SEQ ID NO:2 and SEQ ID NO:46 in an amount effective to induce said immune response against *Ehrlichia canis* in said subject.

2. The method of claim 1, wherein said recombinant protein is encoded by a gene comprising a sequence selected from the group consisting of SEQ ID NO:1 and SEQ ID NO:45.

3. The method of claim 1, wherein said composition comprising a 28-kDa antigen is dispersed in a pharmaceutically acceptable carrier.

* * * * *